(12) United States Patent
Christensen et al.

(10) Patent No.: US 11,905,336 B2
(45) Date of Patent: Feb. 20, 2024

(54) MODIFIED PEPTIDE FRAGMENTS OF CAV-1 PROTEIN AND THE USE THEREOF IN THE TREATMENT OF FIBROSIS

(71) Applicant: Lung Therapeutics, Inc., Austin, TX (US)

(72) Inventors: Dale Christensen, Austin, TX (US); John J. Koleng, Austin, TX (US)

(73) Assignee: Lung Therapeutics, Inc., Austin, TX (US)

(*) Notice: Subject to any disclaimer, the term of this patent is extended or adjusted under 35 U.S.C. 154(b) by 0 days.

(21) Appl. No.: 17/274,721

(22) PCT Filed: Sep. 10, 2019

(86) PCT No.: PCT/US2019/050332
§ 371 (c)(1),
(2) Date: Mar. 9, 2021

(87) PCT Pub. No.: WO2020/055812
PCT Pub. Date: Mar. 19, 2020

(65) Prior Publication Data
US 2021/0347820 A1    Nov. 11, 2021

Related U.S. Application Data

(60) Provisional application No. 62/728,997, filed on Sep. 10, 2018.

(51) Int. Cl.
*A61K 45/06* (2006.01)
*C07K 7/08* (2006.01)
(Continued)

(52) U.S. Cl.
CPC ............... *C07K 7/06* (2013.01); *A61K 45/06* (2013.01); *C07K 7/08* (2013.01); *C07K 14/705* (2013.01); *A61K 38/00* (2013.01); *C07K 2319/10* (2013.01)

(58) Field of Classification Search
CPC .... C07K 7/06; C07K 2319/10; C07K 14/705; C07K 7/08; A61K 38/00; A61K 45/06
See application file for complete search history.

(56) References Cited

U.S. PATENT DOCUMENTS

| 4,021,387 A | 5/1977 | Goetzl et al. |
| 4,554,101 A | 11/1985 | Hopp |

(Continued)

FOREIGN PATENT DOCUMENTS

| CN | 101022830 A | 8/2007 |
| CN | 102387784 A | 3/2012 |

(Continued)

OTHER PUBLICATIONS

Chen, X., et al., Fusion protein linkers: Property, design and functionality, Advanced Drug Delivery Reviews; 65: 1357-1369. (Year: 2013).*

(Continued)

*Primary Examiner* — Melissa L Fisher
*Assistant Examiner* — John Michael Cronin
(74) *Attorney, Agent, or Firm* — COOLEY LLP

(57) ABSTRACT

Provided herein are compositions comprising modified caveolin-1 (Cav-1) peptides. Further provided are methods of using the modified Cav-1 peptides for the treatment of lung infections or acute or chronic lung injury, particularly lung fibrosis.

11 Claims, 1 Drawing Sheet

Specification includes a Sequence Listing.

(51) Int. Cl.
*C07K 14/705* (2006.01)
*A61K 38/00* (2006.01)
*C07K 7/06* (2006.01)

(56) References Cited

U.S. PATENT DOCUMENTS

| | | | |
|---|---|---|---|
| 4,628,045 | A | 12/1986 | Hahn |
| 4,719,288 | A | 1/1988 | Fuhrer et al. |
| 4,816,449 | A | 3/1989 | Hahn |
| 5,277,175 | A | 1/1994 | Riggs et al. |
| 5,284,133 | A | 2/1994 | Burns et al. |
| 5,299,566 | A | 4/1994 | Davis et al. |
| 5,355,872 | A | 10/1994 | Riggs et al. |
| 5,358,934 | A | 10/1994 | Borovsky et al. |
| 5,559,209 | A | 9/1996 | Nishimoto |
| 5,660,166 | A | 8/1997 | Lloyd et al. |
| 5,728,680 | A | 3/1998 | Morozov et al. |
| 5,797,389 | A | 8/1998 | Ryder |
| 5,823,179 | A | 10/1998 | Grychowski et al. |
| 5,889,155 | A | 3/1999 | Ashkenazi et al. |
| 6,016,974 | A | 1/2000 | Mascitelli |
| 6,017,735 | A | 1/2000 | O'Hare et al. |
| 6,041,776 | A | 3/2000 | Briggs, III |
| 6,044,841 | A | 4/2000 | Verdun et al. |
| 6,126,939 | A | 10/2000 | Eisenbach-Schwartz et al. |
| 6,241,159 | B1 | 6/2001 | Ganan-Calvo et al. |
| 6,261,569 | B1 | 7/2001 | Comis et al. |
| 6,354,516 | B1 | 3/2002 | Patel et al. |
| 6,357,671 | B1 | 3/2002 | Cewers |
| 6,921,020 | B2 | 7/2005 | Ivri |
| 6,926,208 | B2 | 8/2005 | Ivri |
| 6,968,840 | B2 | 11/2005 | Smith et al. |
| 6,978,941 | B2 | 12/2005 | Litherland et al. |
| 7,040,549 | B2 | 5/2006 | Ivri et al. |
| 7,083,112 | B2 | 8/2006 | Ivri |
| 7,104,463 | B2 | 9/2006 | Litherland et al. |
| 7,332,469 | B2 | 2/2008 | Idell |
| 7,360,536 | B2 | 4/2008 | Patel et al. |
| 7,494,976 | B2 | 2/2009 | Sessa |
| 8,058,227 | B2 | 11/2011 | Hoffman et al. |
| 8,349,798 | B2 | 1/2013 | Sessa |
| 8,487,072 | B2 | 7/2013 | Beliveau et al. |
| 8,697,840 | B2 | 4/2014 | Shetty et al. |
| 9,630,990 | B2 | 4/2017 | Shetty et al. |
| 9,908,915 | B2 | 3/2018 | Sessa et al. |
| 10,377,796 | B2 | 8/2019 | Shetty et al. |
| 10,550,151 | B2 * | 2/2020 | Sessa ............ C07K 7/06 |
| 11,161,875 | B2 * | 11/2021 | Shetty ............ C07K 7/06 |
| 2002/0020409 | A1 | 2/2002 | Kidwell et al. |
| 2002/0020412 | A1 | 2/2002 | Gilbert et al. |
| 2002/0077283 | A1 | 6/2002 | Sessa |
| 2003/0113271 | A1 | 6/2003 | Katyama et al. |
| 2003/0165510 | A1 | 9/2003 | Sessa |
| 2004/0175384 | A1 | 9/2004 | Mohapatra et al. |
| 2007/0098721 | A1 | 5/2007 | Hillen et al. |
| 2007/0140976 | A1 | 6/2007 | Chen et al. |
| 2007/0154404 | A1 | 7/2007 | Colombo et al. |
| 2009/0075875 | A1 | 3/2009 | Hoffman et al. |
| 2009/0134235 | A1 | 5/2009 | Ivri |
| 2009/0227515 | A1 | 9/2009 | Shetty et al. |
| 2009/0304666 | A1 | 12/2009 | Harrison et al. |
| 2011/0218152 | A1 | 9/2011 | Beliveau et al. |
| 2011/0301142 | A1 | 12/2011 | Hutchinson et al. |
| 2012/0014917 | A1 | 1/2012 | Kossen et al. |
| 2013/0224163 | A1* | 8/2013 | Head ............ C12N 15/86 424/93.21 |
| 2015/0141340 | A1 | 5/2015 | Sessa |
| 2016/0022577 | A1 | 1/2016 | Flynn et al. |
| 2016/0272678 | A1 | 9/2016 | Shetty et al. |
| 2016/0279209 | A1 | 9/2016 | Williams et al. |
| 2017/0112898 | A1 | 4/2017 | Liu |
| 2017/0128520 | A1 | 5/2017 | Eveleth et al. |
| 2017/0253632 | A1 | 9/2017 | Shetty et al. |
| 2018/0050084 | A1 | 2/2018 | Williams, III et al. |
| 2018/0086791 | A1 | 3/2018 | Shetty et al. |
| 2019/0062836 | A1 | 2/2019 | Abbas et al. |
| 2020/0164028 | A1 | 5/2020 | Williams et al. |
| 2020/0165298 | A1 | 5/2020 | Shetty et al. |
| 2020/0384034 | A1 | 12/2020 | Glassberg Csete et al. |
| 2021/0260150 | A1 | 8/2021 | Williams, III et al. |
| 2021/0330741 | A1 | 10/2021 | Williams, III et al. |
| 2022/0098239 | A1 | 3/2022 | Shetty et al. |
| 2022/0160814 | A1 | 5/2022 | Wasnick et al. |
| 2022/0276652 | A1 | 9/2022 | Kyono et al. |
| 2022/0370544 | A1 | 11/2022 | Shetty |
| 2023/0159608 | A1 | 5/2023 | Windsor |
| 2023/0212223 | A1 | 7/2023 | Christensen et al. |

FOREIGN PATENT DOCUMENTS

| | | | |
|---|---|---|---|
| CN | 102753148 A | | 10/2012 |
| CN | 107216394 A | * | 9/2017 ............ C07K 14/47 |
| CN | 111671886 A | | 9/2020 |
| EP | 0 097 994 | | 9/1987 |
| EP | 1 076 091 A1 | | 2/2001 |
| JP | 2001509515 A | | 7/2001 |
| JP | 2012250981 A | | 12/2012 |
| WO | WO 01/11038 | | 2/2001 |
| WO | WO 02/20768 | | 3/2002 |
| WO | WO 02/20768 A2 | | 3/2002 |
| WO | WO 03/016540 | | 2/2003 |
| WO | WO 2008/046228 | | 4/2008 |
| WO | WO 2009/074634 | | 6/2009 |
| WO | WO 2009/111625 A2 | | 9/2009 |
| WO | WO-2009152453 A2 | | 12/2009 |
| WO | WO 2010/030813 | | 3/2010 |
| WO | WO 2010/048275 A2 | | 4/2010 |
| WO | WO 2011/098552 | | 8/2011 |
| WO | WO 2013/184482 | | 12/2013 |
| WO | WO 2014/145389 A1 | | 9/2014 |
| WO | WO-2015000371 A1 | | 1/2015 |
| WO | WO 2015/066664 | | 5/2015 |
| WO | WO 2015/080943 | | 6/2015 |
| WO | WO 2015/080980 | | 6/2015 |
| WO | WO 2016/138413 A1 | | 9/2016 |
| WO | WO 2020/055812 A1 | | 3/2020 |
| WO | WO 2020/055824 A1 | | 3/2020 |
| WO | WO-2020106922 A1 | | 5/2020 |
| WO | WO 2020/185826 A1 | | 9/2020 |
| WO | WO-2021216659 A1 | | 10/2021 |
| WO | WO-2021257816 A2 | | 12/2021 |
| WO | WO-2022182949 A2 | | 9/2022 |
| WO | WO-2022266410 A1 | | 12/2022 |
| WO | WO-2023070069 A1 | | 4/2023 |

OTHER PUBLICATIONS

Altman et al., "Predictors of survival in systemic sclerosis (scleroderma)", Arthritis Rheum., 34:403-413, 1991.

Anderson, "The caveolae membrane system", Annu Rev Biochem, 67:199-225, 1998.

Arbuzova et al., "Membrane Binding of Peptides Containing Both Basic and Aromatic Residues—Experimental Studies with Peptides Corresponding to the Scaffolding Region of Caveolin and the Effector Region of MARCKS", Biochemistry, 39(33) 10330-9, 2000.

Bellini et al., "The role of the fibrocytes, a bone marrow-derived mesenchymal progenitor, in reactive and reparative fibrosis", Lab Invest, 2007, 13 pages.

Beon et al., "Myofibroblast induction and microvascular alteration in scleroderma lung fibrosis", Clin Exp Rheumatol, 22: 733-742, 2004.

Bernatchez et al., "Dissecting the molecular control of endothelial NO synthase by caveolin-1 using cell-permeable peptides", Proc Natl Acad Sci USA, 102:761-766, 2005.

Bhandary et al., "Regulation of alveolar epithelial cell apoptosis and pulmonary fibrosis by coordinate expression of components of the fibrinolytic system", Am J Physiol Lung Cell Mal Physiol., 302:L463-L473, 2012.

Bogatkevich et al., "Contractile Activity and Smooth Muscle alpha-actin organization in thrombin-induced human lung myofibroblasts", J Physiol Lung Cell Mol Physiol, 85:L334-L343, 2003.

(56) References Cited

OTHER PUBLICATIONS

Bogatkevich et al., "Thrombin differentiates normal lung fibroblasts to a myofibroblast phenotype via the proteolytically activated receptor-1 and a protein kinase C-dependent pathway", J Biol Chem., 276:45184-45192, 2001.
Bowie et al., "Deciphering the message in protein sequences: tolerance to amino acid substitutions", Science, 247: 1306-1310, 1990.
Bucci et al., "In vivo delivery of the caveolin-1 scaffolding domain inhibits nitric oxide synthesis and reduces inflammation", Nature Med, 6:1362-1367, 2000.
Bussone et al., "Interstitial lung disease in systemic sclerosis", Autoimmunity Reviews, 10:248- 255, 2011.
Carvalho et al., "Influence of particle size on regional lung deposition—What evidence is there?" Int. J Pharma. 406: 1-10, 2011.
CAS RN 246246-98-9. STN Entry Date Dec. 31, 1998, 1 page.
Cohen et al., "Caveolin-1 null mice develop cardiac hypertrophy with hyperactivation of p42/44 MAP kinase in cardiac fibroblasts", Am J Physiol Cell Physiol., 284:C457-474, 2003.
Couet et al., "Identification of peptide and protein ligands for the caveolin-scaffolding domain—Implications for the interaction of caveolin with caveolae-associated proteins", J Biol Chem., 272:6525-6533, 1997.
Couet et al., "Interaction of a receptor tyrosine kinase, EGF-R, with caveolins—Caveolin binding negatively regulates tyrosine and serine/threonine kinase activities", J Biol Chem., Biol Chem., 272:6525-6533, 1997.
Cui et al., "Identification of specific domain responsible for JNK2alpha2 autophosphorylation", J Biol. Chem., 280:9913-9920, 2005.
De la Torre et al., "On choosing the right ether for peptide precipitation after acid cleavage," Journal of Peptide Science, 14(3), 360-363, 2008.
Drab et al., "Loss of caveolae, vascular dysfunction, and pulmonary defects in caveolin-1 gene-disrupted mice", Science, 293:2449-2452, 2001.
Epand et al., "Caveolin Scaffolding Region and Cholesterol-rich Domains in Membranes," Journal of Molecular Biology, 345(2): 339-350, 2005.
Extended European Search Report issued in European Patent Application No. 14762435.7, dated Nov. 17, 2016, 17 pages.
Finch et al., "Bleomycin-induced scleroderma", J Rheumatol, 7:651-659, 1980.
Galbiati et al., "Expression of caveolin-1 and -2 in differentiating PC12 cells and dorsal root ganglion neurons: caveolin-2 is up-regulated in response to cell injury", Proc Natl Acad Sci USA, 95:10257-10262, 1998.
Gallelli et al. "Severe Acute Lung Injury Related to COVID-19 Infection: A Review and the Possible Role for Escin," J Clin Pharmacol, May 22, 2020 (May 22, 2020), vol. 60, p. 815-825.
Gardenhire et al., "A guide to aerosol delivery devices for respiratory therapists," American Association for Respiratory Care (2013): 1-56.
Gralinski et al. "Mechanisms of severe acute respiratory syndrome coronavirus-induced acute lung injury," mBio, Aug. 6, 2013 (Aug. 6, 2013), vol. 4, e00271-13, pp. 1-12.
Gray et al., "Partially degraded fibrin (ogen) stimulates fibroblast proliferation in vitro", Am J Resvirator Cell Mol Biol., 12: 684-690, 1995.
Gunther A et al., "Prevention of Bleomycin-induced Lung Fibrosis by Aerosolization of Heparin or Urokinase in Rabbits", American Journal of Respiratory and Critical Care Medicine, American Lung Association, New York, Ny, US, vol. 168, No. 11, Dec. 1, 2003 (Dec. 1, 2003), pp. 1358-1365.
Guo et al., "Involvement of caveolin-1 in the Jak-Stat signaling pathway and infectious spleen and kidney necrosis virus infection in mandarin fish (*Siniperca chua tsi*)," Molecular Immunology, 48(8): 992-1000, 2011.
Hartmann et al., "TIP peptide inhalation in experimental acute lung injury: effect of repetitive dosage and different synthetic variants," BMC anesthesiology 14.1 (2014): 42.

Herold et al. "Influenza virus-induced lung injury: pathogenesis and implications for treatment," Eur Respir J, Mar. 18, 2015 (Mar. 18, 2015), vol. 45, pp. 1463-1478.
Hiemenz, "Principles of colloid and surface chemistry, 2nd edition" (1986) ISBN 0-8247-7 476-0, 5 pages.
Hocke et al. "Emerging human middle East respiratory syndrome coronavirus causes widespread infection and alveolar damage in human lungs," Am J Respir Crit Care Med, Oct. 1, 2013 (Oct. 1, 2013), vol. 188, pp. 882-886.
Hong et al., "Differentiation of human circulating fibrocytes as mediated by transforming growth factor-beta and peroxisome proliferators activated receptor-gamma", J Biol Chem, 2007, 282:22910-22920.
Horton et al., "Phase behavior and the partitioning of caveolin-1 scaffolding domain peptides in model lipid bilayers," Journal of Colloid and Interface Science, 304(1): 67-76, 2006.
Hua et al., "Endothelin-1 activates mesangial cell ERK1/2 via EGF-receptor transactivation and caveolin-1 interaction", Am J Physiol Renal Physiol, 284:F303-312, 2003.
Huang et al., Reduced transcriptional activity in the p53 pathway of senescent cells revealed by the MDM2 antagonist nutlin-3, Aging, 2009, 1(10), 845-54.
Hubner, R.-H et al., "Standardized quantification of pulmonary fibrosis in histological samples," Biotechniques, 44, 507-11, 514-7, 2008.
International Preliminary Report on Patentability issued in International Application No. PCT/US2014/030147, dated Sep. 24, 2015, 9 pages.
International Search Report and Written Opinion issued in International Application No. PCT/US2014/030147, dated Aug. 6, 2014, 16 pages.
International Preliminary Report on Patentability issued in International Application No. PCT/US2016/019827, dated Aug. 29, 2017, 7 pages.
International Search Report and Written Opinion issued in International Application No. PCT/US2016/019827, dated May 25, 2016, 12 pages.
International Preliminary Report on Patentability issued in corresponding PCT Application No. PCT/ US2019/050349, dated Mar. 25, 2021, 10 pages.
International Search Report and Written Opinion issued in corresponding PCT Application No. PCT/US2019/050349, dated Dec. 11, 2019, 18 pages.
International Search Report and Written Opinion dated Dec. 7, 2021, in International Application No. PCT/US2021/037812, 14 pages.
Kasper et al., "Loss of caveolin-1 expression in type I pneumocytes as an indicator of subcellular alterations during lung fibrogenesis", Histochem Cell Biol, 109:41-48, 1998.
Kim et al., "Alveolar epithelial cell mesenchymal transition develops in vivo during pulmonary fibrosis and is regulated by the extracellular matrix", Proc Natl Acad Sci USA, 103: 13180-13185, 2006.
Le Saux et al., "Down-regulation of caveolin-1, an inhibitor of transforming growth factor-β signaling, an acute allergen-induced airway remodeling", The Journal of Biological Chemistry, 283(9): 5760-5768, 2008.
Levin et al., "Double barrel shotgun scanning of the caveolin-1 scaffolding domain", ACS Chemical Biology, 2(7): 493-500, 2007.
Lisanti et al., "Characterization of caveolin-rich membrane domains isolated from an endothelial-rich source: implications for human disease", J Biol Chem, 126: 111-126, 1994.
Mimura et al., "Constitutive phosphorylation of focal adhesion kinase is involved in the myofibroblast differentiation of scleroderma fibroblasts", J Invest Dermatol, 124: 886-892, 2005.
Moore et al., "CCR2-mediated recruitment of fibrocytes to the alveolar space after fibrotic injury", Am J Pathol, 166: 675-684, 2005.
Muller et al., "Redistribution of glycolipid raft domain components induces insulinmimetic signaling in rat adipocytes", Mol Cell Biol., 21:4553-4567, 2001.

(56) References Cited

OTHER PUBLICATIONS

Odajima et al., "Loss of caveolin-1 in bronchiolization in lung fibrosis", Journal of Histochemistry & Cytochemistry, 55(9): 899-909, 2007.
Oka et al., "Caveolin interaction with protein kinase C", J Biol Chem, 272:33416-33421, 1997.
Okamoto et al., "Caveolins, a family of scaffolding proteins for organizing 'pre-assembled signaling complexes' at the plasma membrane", J Biol Chem, 273:5419-5422, 1998.
Osier et al., "Intratracheal Inhalation vs Intratracheal Instillation: Differences in Particle Effects," Fundam. Appl. Toxicol., 40:220-227, 1997.
Palmer, Brian; "The science of sea spray", dated May 21, 2015, downloaded from https://www.nrdc.org/onearth/science-sea-spray, on Oct. 25, 2018, 7 pages.
Pannu et al., "Transforming Growth Factor-beta receptor type I-dependent fibrogenic gene programls mediated via activation of Smad1 and ERK1/2 pathways", J Biol Chem, 282: 10405-10413, 2007.
Phillips et al., "Circulating fibrocytes traffic to the lungs in response to CXCL 12 and mediate fibrosis", J Clin Invest, 114: 438-446, 2004.
Quan et al., "The role of the circulating fibrocytes in fibrosis", Curr Rheumatol Rep, 8: 145-150, 2006.
Razani et al., "Caveolae: from cell biology to animal physiology", Pharmacal Rev, 54:431-467, 2002.
Razani et al., "Caveolin-1 null mice are viable but show evidence of hyperproliferative and vascular abnormalities", J Biol Chem., 276:38121-38138, 2001.
Razani et al., "Regulation of CAMP-mediated signal transduction via interaction of caveolins with the catalytic subunit of protein kinase A", J Biol Chem., 274:26353-26360, 1999.
Respaud et al., "Effect of formulation on the stability and aerosol performance of a nebulized antibody." MAbs. vol. 6. No. 5. 1347-1355. Taylor & Francis. 2014.
"Retsch technology sales literature for light scatterers", downloaded from https://www.retsch-technology.com/products/laser-light-scattering/, on Jun. 11, 2019, 5 pages.
Rybin et al., "Activated protein kinase C isoforms target to cardiomyocyte caveolae: stimulation of local protein phosphorylation", Circ Res, 84: 980-988, 1999.
Scherer et al., "Caveolin isoforms differ in their N-terminal protein sequence and subcellular distribution. Identification and epitope mapping of an isoform-specific monoclonal antibody probe", J Biol Chem., 270: 16395-16401, 1995.
Sedding et al., "Caveolin-1 facilitates mechanosensitive protein kinase B (Akt) signaling in vitro and in vivo", Circ Res, 96: 635-642, 2005.
Sharma et al., "Bleomycin-induced scleroderma", JAPI, 52:76-77, 2004.
Shaul et al., "Role of plasmalemmal caveolae in signal transduction", AJP Lung Cell Mol Phys, 275:L843-L851, 1998.
Shetty et al., "Regulation of Airway and Alveolar Epithelial Cell Apoptosis by p53-Induced Plasminogen Activator Inhibitor-1 during Cigarette Smoke Exposure Injury", Am J Respir Cell Mol Biol, 47/4, pp. 474-483, 2012.
Shi-Wen et al., "Constitutive ALK5-independent c-Jun N-Terminal Kinase activation contributes toendothelin-1 overexpression in pulmonary fibrosis: evidence of an autocrine endothelin loop operating through the endothelin A and B receptors", Mol Cell Biol, 26; 5518-5527, 2006.
Shi-Wen et al., "Endothelin-1 promotes myofibroblast induction through the ETA receptor via arac/Phosphoinositide 3-kinase/Akt-dependent pathway and is essential for the enhanced contractile phenotype of fibrotic fibroblasts", MBC, 15: 2707-2719, 2004.
Silver, "Interstitial lung disease of systemic sclerosis", Int Rev Immunol., 12:281-291, 1995.
Song et al., "Co-precipitation and direct interaction of Ras with caveolin, an integral membrane protein of caveolae microdomains", J Biol Chem, 271:9690-9697, 1996.
Sowa et al., "Distinction between signaling mechanisms in lipid rafts vs. caveolae", Proc Natl Acad Sci USA, 98: 14072-14077, 2001.
Steen et al., "Changes in causes of death in systemic sclerosis", Ann Rheum Dis, 66: 940-944, 2007.
Surasarang et al., "Formulation for a Novel Inhaled Peptide therapeutic for Idiopathic Pulmonary Fibrosis," Drug Dev. Ind. Pharm., 44(2):184-198, 2018.
Tashkin et al., "Cyclophosphamide versus placebo in scleroderma lung disease", N Engl J Med,354:2655-2666, 2006.
Tepper, J. S.; Kuehl, P. J.; Cracknell, S.; Nikula, K. J.; Pei, L.; Blanchard, J. D. SymposiumSummary: "Breathe In, Breathe Out, Its Easy: What You Need to Know about Developing Inhaled Drugs." Int. J Toxicol. 35, 376-392, 2016.
Thannickal et al., "Myofibroblast differentiation by transforming growth factor-beta 1 is dependenton cell adhesion and integrin signaling via focal adhesion kinase", J Biol Chem, 278: 12384-12389, 2003.
Toker et al., "Akt/Protein Kinase B regulated by autophosphorylation in the hypothetical PDK-2 site", J Biol Chem, 275: 8271-8274, 2000.
Tourkina et al., "Anti-fibrotic and anti-inflammatory roles of caveolin-1 in scleroderma", ASCB Meeting, San-Diego, Dec. 2006, Abstract L66, 1 page.
Tourkina et al., "Antifibrotic properties of caveolin-1 scaffolding domain in vitro and in vivo", Am J Physiol Lung Cell Mol Physiol., 294: L843-L861, 2008.
Tourkina et al., "Caveolin-1 regulates collagen expression through MEKIERK signaling anddifferentiation normal lung fibroblasts in myofibroblasts", ASCB Meeting, Washington, DC, Dec. 2005, Abstract 370, 1 page.
Tourkina et al., "Curcumin-induced apoptosis in scleroderma lung fibroblasts: Role of protein kinase Ce", American Journal of Respiratory Cellular and Molecular Biology, 31:28-35, 2004.
Tourkina et al., "Depletion of PKC-epsilon in normal and scleroderma lung fibroblasts has opposite effects on tenascin expression", Arthritis and Rheum, 44:1370-1381, 2001.
Tourkina et al., "Opposing effects of protein kinase C alpha and protein kinase C epsilon oncollagen expression by human lung fibroblasts are mediated via MEKIERK and caveolin-1 signaling", J Biol Chem, 280:13879-13887, 2005.
Uhal et al., "Alveolar epithelial cell death adjacent to underlying myofibroblasts in advanced fibrotic human lung", Am J Physiol Lung Cell Mol Physiol, 275:L 1192-L1199, 1998.
Van de Water et al., "Animal models of scleroderma: contrasts and comparisons", Intern Rev Immunol, 12:201-216, 1995.
Vassilev et al., "In Vivo Activation of the p3 Pathway by Small-Molecule Antagonists of MDM2," Science, 303:844-848, 2004.
Vyalov et al., "Rat alveolar myofibroblasts acquire alpha-smooth muscle actin expression during bleomycin-induced pulmonary fibrosis", Am J Pathol, 143: 1754-1765, 1993.
Wanaski et al., "Caveolin Scaffolding Region and the Membrane Binding Region of Src Form Lateral Membrane Domains", Biochemistry. 42(1) 42-56, 2003.
Wang et al., "Caveolin-1: a critical regulator of lung fibrosis in idiopathic pulmonary fibrosis", J Exp Med, 203; 2895-2906, 2006.
Wells, "Additivity of mutational effects in proteins", Biochemistry, 29: 8509-8517, 1990.
Wender et al., "The design, synthesis, and evaluation of molecules that enable or enhance cellular uptake: peptoid molecular transporters", Proc Natl Acad Sci USA, 97: 13003-13008, 2000.
White et al., "Negative regulation of myofibroblast differentiation by PTEN (Phosphatase and Tensin Homolog deleted on chromosome 10)", Am J Respir Crit Care Med., 173:112- 121, 2006.
Wu et al., "Detection of epithelial to mesenchymal transition in airways of a bleomycin induced pulmonary fibrosis model derived from an alpha-smooth muscle actin-Cre transgenic mouse", Respir Res., 8:1, 2007, 11 pages.
Yamamoto et al., "Animal model of sclerotic skin 1: local injections of bleomycin induce sclerotic skin mimicking scleroderma", J Invest Dermatol., 112:456-462, 1999.

(56) References Cited

OTHER PUBLICATIONS

Zhang et al., "Lung fibroblast alpha-smooth muscle actin expression and contractile phenotype in bleomycin-induced pulmonary fibrosis", Am J Pathol, 148:527-537, 1996.
Extended European Search Report issued in European Patent Application No. 21168926.0, dated Nov. 10, 2021, 6 pages.
Extended European Search Report issued in European Patent Application No. 19859759.3, dated May 17, 2022, 11 pages.
International Search Report and Written Opinion dated Sep. 9, 2021, in International Application No. PCT/US2021/028326, 9 pages.
Marudamuthu, A.S., et al., "Caveolin-1-Derived Peptide Limits Development of Pulmonary Fibrosis," Science translational medicine, Dec. 11, 2019, vol. 11(522), 16 pages.
Agu et al., "The lung as a route for systemic delivery of therapeutic proteins and peptides," Respir Res. Apr. 12, 2001;2(4):198-209.
Anonymous: "Caveolin-1 scaffolding domain peptide—ALX-153-064—Enzo Life Sciences", Aug. 28, 2018 (Aug. 28, 2018), pp. 1-2, XP055919016, Retrieved from the Internet: URL: http://web.archive.org/web/20180828064451/https://www.enzolifesciences.com/ALX-153-064/caveolin-1-scaffolding-domain-peptide/ [retrieved on May 9, 2022].
Campo et al., A Large Kindred of Pulmonary Fibrosis Associated With a Novel ABCA3 gene variant, Respiratory Research, 2014, vol. 15, No. 43, p. 1-15.
Dhand R., "Nebulizers That Use a Vibrating Mesh or Plate With Multiple Apertures to Generate Aerosol", Respiratory Care, Dec. 2002, vol. 47(12), pp. 1406-1416.
Hertel et al., "Protein stability in pulmonary drug delivery via nebulization," Advanced Drug Delivery Reviews 93 (2015) 79-94.
Irngartinger, M., et al., "Pulmonary Delivery of Therapeutic Peptides via Dry Powder Inhalation: Effects of Micronisation and Manufacturing," European Journal of Pharmaceutics and Biopharmaceutics, Jul. 2004, vol. 58(1), pp. 7-14, XP004519822.
Itoga et al., "Factors Affecting Nebulized Albuterol Aerosol Particle Sizes", Annals of Emergency Medicine, Oct. 1, 2013, vol. 62(4), 2 pages.
Jin, Y et al., "Caveolin-1: a critical regulator of lung injury", American Journal of Physiology, Lung Cellular and Molecular Physiology, Feb. 2011, E pub Nov. 19, 2010, vol. 300, No. 2; pp. L151-L157.
Korfei, et al., "The ageing lung under stress," Eur Respir Rev, Jul. 7, 2020, vol. 29(156), 200126, 22 pages.
Myers et al., "The science guiding selection of an aerosol delivery device", Respiratory care, Nov. 1, 2013, vol. 58(11), pp. 1963-1973.
Nagaraja et al., "p53 Expression in Lung Fibroblasts Is Linked to Mitigation of Fibrotic Lung Remodeling," The American Journal of Pathology, Oct. 2018, vol. 188(10), pp. 2207-2222.
Nalbandian A., et al., "Post-acute COVID-19 syndrome" Nature Medicine, Mar. 22, 2021, vol. 27, pp. 601-615.
Schmitz, M., et al., "Effect of Cavtratin, a Caveolin-1 Scaffolding Domain Peptide, on Oligodendroglial Signaling Cascades," Cellular and Molecular Neurobiology, Oct. 2011, vol. 31 (7), pp. 991-997, XP019955941.
Shetty et al., "Physical stability of dry powder inhaler formulations," Expert Opin Drug Deliv. Jan. 2020; 17(1): 77-96.
Tiwari et al.,"p53- and PAI-1-Mediated Induction of C-X-C Chemokines and CXCR2: Importance in Pulmonary Inflammation due to Cigarette Smoke Exposure," American Journal of Physiology Lung Cellular and Molecular Physiology, Jan. 2016, vol. 310(6), pp. 496-506.
U.S. Appl. No. 17/499,859, which is a Continuation of U.S. Appl. No. 17/499,859.
Vandana, K.R., et al., "An Overview on in Situ Micronization Technique—an Emerging Novel Concept in Advanced Drug Delivery," Saudi Pharmaceutical Journal, Sep. 2014, vol. 22 (4), pp. 283-289, XP055293544.
Wang, Y., et al., "Mydgf Promotes Cardiomyocyte Proliferation and Neonatal Heart Regeneration", Theranostics, Jul. 11, 2020, vol. 10, No. 20; pp. 1-3.
Zhang. Y. et al., "Development of an Excipient-Free Peptide Dry Powder Inhalation for the Treatment of Pulmonary Fibrosis", Molecular Pharmaceutics, Jan. 8, 2020, XP055919000, 13 pages.
Bonelli et al., "Solid phase synthesis of retro-inverso peptide analogues," Int. J. Peptide Protein Res. 24(6), Apr. 26, 1984, pp. 553-556.
Bordo et al., "Suggestions for "Safe" Residue Substitutions in Site-directed Mutagenesis," Journal of Molecular Biology, vol. 217, Issue 4, Feb. 20, 1991, pp. 721-729.
French et al., "What is a Conservative Substitution?," J Mol. Evol. (1983) 19: 171-175.
Fults et al., "The influence of sampling chamber dimensions on aerosol particle size measurement by cascade impactor and twin irnpinger," J. Pharm. Pharmacol. 1991,43: 726-728.
Giannis et al., "Peptidomimetics in Drug Design," Advances in Drug Research, vol. 29, 1997, pp. 1-78.
Hruby, "Conformational and Topographical Considerations in the Design of Biologically Active Peptides," Biopolymers, vol. 33: 1073-1082 (1993).
Kyte et al., "A Simple Method for Displaying the Hydropathic Character of a Protein," J. Mol. Biol. (1982) 157, 105-132.
Matthay et al., "The acute respiratory distress syndrome," The Journal of Clinical Investigation, vol. 122, No. 8, Aug. 2012, pp. 2731-2740.
McLean et al., "Optical Patternation: A Technique for Three-Dimensional Aerosol Diagnostics," Analytical Chemistry, vol. 72, No. 20, Oct. 15, 2000, pp. 4796-4804.
Meyer et al., An international ISHLT/ATS/ERS clinical practice guideline: diagnosis and management of bronchiolitis obliterans syndrome, Eur. Respir. J., Oct. 30, 2014: 44: pp. 1479-1503.
Mitchell et al., A New Synthetic Route to tert-Butyloxycarbonylaminoacyl-4-(oxymethyl)phenylacetamidomethyl-resin, an Improved Support for Solid-Phase Peptide Synthesis, J. Org. Chem., vol. 43, No. 14, 1978, pp. 2845-2852.
Moore et al., "Design and Pharmacology of Peptide Mimetics," Advances in Pharmacology, vol. 33, pp. 91-141 (1995).
Office Action dated Feb. 2, 2021, for Chinese Application No. 201680012611.5, 22 pages (pp. 1-11, English translation; pp. 12-22 pages, original).
Quanlin Li, "New medicine development and research", China Medical Science Press, published on Dec. 31, 2008; pp. 668-669, paragraph 4, pp. 674, pp. 675-676.
Rabe et al., "Global Strategy for the Diagnosis, Management, and Prevention of Chronic Obstructive Pulmonary Disease," Am. J. Respir. Crit. Care Med., vol. 176, May 16, 2007, pp. 532-555.
Ralston et al., "Clinical Practice Guideline: The Diagnosis, Management, and Prevention of Bronchiolitis," Pediatrics, vol. 134, No. 5, Nov. 2014, 31 pages.
Schellenberger et al., "A recombinant polypeptide extends the in vivo half-life of peptides and proteins in a tunable manner," Nature Biotechnology, vol. 27, No. 12, Dec. 2009, 7 pages.
Shetty et al., "Induction of p53 by Urokinase in Lung Epithelial Cells," The Journal of Biological Chemistry, vol. 280, No. 30, Issue of Jul. 29, pp. 28133-28141, 2005.
Singh et al., "Transdermal Drug Delivery by Passive Diffusion and Iontophoresis: A Review," Medicinal Research Reviews, vol. 13, No. 5, 569-621 (1993).
Taylor, "The Classification of Amino Acid Conservation," J. Theor. Biol. 119 (1986), pp. 205-218.
Tsushima et al., "Acute Lung Injury Review," Inter. Med. 48: 621-630, 2009.
Vecellio None et al., "Validation of Laser Diffraction Method as a Substitute for Cascade Impaction in the European Project for a Nebulizer Standard," Journal of Aerosol Medicine, vol. 14, No. 1, 2001, pp. 107-114.
Verdini et al., "Synthesis, Resolution, and Assignment of Configuration of Potent Hypotensive Retro-inverso Bradykinin Potentiating Peptide 5a (BPP5A) Analogues," J. Chem. Soc. Perkin Trans., 1, pp. 697-701 (1985).
Waldrep et al., "Advanced Nebulizer Designs Employing Vibrating Mesh/Aperture Plate Technologies for Aerosol Generation," Current Drug Delivery, 2008, vol. 5, No. 2, pp. 114-119.

(56) References Cited

OTHER PUBLICATIONS

Wawrzynczak et al., "Effect of chemical linkage upon the stability and cytotoxic activity of A chain immunotoxins," Frankel A.E. (eds) Immunotoxins. Cancer Treatment and Research, vol. 37, 1988, 13 pages.
Weinberger, "Airways Reactivity in Patients with CF," Clinical Reviews in Allergy and Immunology, vol. 23, 2002, 10 pages.
Wiley et al., "Peptidomimetics Derived from Natural Products," Medicinal Research Reviews, vol. 13, No. 3, pp. 327-384 (1993).
Abdollahi, et al., "Inhibition of platelet-derived growth factor signaling attenuates pulmonary fibrosis". J Exp Med. (Mar. 21, 2005); 201(6): 925-935.
Cook and Schafer, "Hiding in Plain Sight: Interleukin-11 Emerges as a Master Regulator of Fibrosis, Tissue Integrity, and Stromal Inflammation". Annu Rev Med. Jan. 27, 2020; 71: 263-276.
Creighton, Protein Biosynthesis, Proteins: Structure and Molecular Properties, W. H. Freeman & Co., San Francisco, pp. 79-86 [1983], 24 pages.
Di Guglielmo, et al., "Distinct endocytic pathways regulate TGF-beta receptor signalling and turnover". Nat Cell Biol. May 2003; 5(5): 410-421.
Didiasova, et al., "When Place Matters: Shuttling of Enolase-1 Across Cellular Compartments". Front Cell Dev Biol. Apr. 26, 2019; 7: 61, 11 pages. eCollection 2019.
Etzerodt et al., "Soluble ectodomain CD163 and extracellular vesicle-associated CD163 are two differently regulated forms of 'soluble CD163' in plasma". Sci Rep. 2017; 7: 40286, 10 pages. Epub Jan. 13, 2017.
Gauldie, et al., "Smad3 Signaling Involved in Pulmonary Fibrosis and Emphysema". Proc Am Thorac Soc. Nov. 2006; 3(8): 696-702.
Gibson, et al., "A novel method for real time quantitative RT-PCR". Genome Res. Oct. 1996; 6(10): 995-1001.
Gvaramia, et al., "Role of caveolin-1 in fibrotic diseases". Matrix Biology (2013); 32(6): 307-315.
Ishikawa, et al., "Hemoglobin a and B are ubiquitous in the human lung, decline in idiopathic pulmonary fibrosis but not in COPD". Respiratory Research 2010; 11, Article No. 123, 13 pages.
Kishi, et al., "Blockade of platelet-derived growth factor receptor-β, not receptor-α ameliorates bleomycin-induced pulmonary fibrosis in mice". PLoS One. Dec. 31, 2018; 13(12): e0209786, 19 pages. eCollection 2018.
Konishi, et al., "Gene expression profiles of acute exacerbations of idiopathic pulmonary fibrosis". Am J Respir Crit Care Med. Jul. 15, 2009; 180(2): 167-175. Epub Apr. 10, 2009.
Korf-Klingebiel, et al., "Myeloid-derived growth factor (C19orf10) mediates cardiac repair following myocardial infarction". Nat Med. Feb. 2015; 21(2): 140-149. Epub Jan. 12, 2015.
Manichaikul, et al., "Plasma Soluble Receptor for Advanced Glycation End Products in Idiopathic Pulmonary Fibrosis". Ann Am Thorac Soc. May 2017; 14(5): 628-635.
Razani, et al., "Caveolin-1 Regulates Transforming Growth Factor (TGF)-b/SMAD Signaling through an Interaction with the TGF-ß Type I Receptor". J Biol Chem. Mar. 2, 2001; 276(9): 6727-3738. Epub Dec. 1, 2000.
Sanders, et al., "Epigenetic Regulation of Caveolin-1 Gene Expression in Lung Fibroblasts". Am J Respir Cell Mol Biol. Jan. 2017; 56(1): 50-61.
Sanders, et al., "SMAD-independent down-regulation of caveolin-1 by TGF-β: effects on proliferation and survival of myofibroblasts". PLoS One. Feb. 6, 2015; 10(2): e0116995, 18 pages. eCollection 2015.
Shitata, et al., "Is There a Potential Therapeutic Role for Caveolin-1 in Fibrosis?" Front. Pharmacol. 2017; 8(1): 567, 8 pages.
Toth et al., "A novel oligopeptide delivery system for poorly absorbed peptides and drugs", Peptides: Chemistry, Structure and Biology, Rivier and Marshal, eds., ESCOM Puhl., Leiden, pp. 1078-1079, 4 pages, 1990.
Tsang, et al., "CP110 cooperates with two calcium-binding proteins to regulate cytokinesis and genome stability". Mol Biol Cell. Aug. 2006; 17(8): 3423-3434. Epub Jun. 7, 2006.
Van Haren, et al., "Bronchodilator response in adult patients with cystic fibrosis: effects on large and small airways," Eur Respir J. Mar. 1991; 4(3): 301-307.
Wawrzynczak and Thorpe, "Methods for Preparing Immunotoxins: Effect of the Linkage on Activity and Stability", Immunoconjugates, Antibody Conjugates in Radioimaging and Therapy of Cancer (1987); ed. Carl-Wilhelm Vogel, M.D., Ph.D., Chapter 3, pp. 28-54, 31 pages.
Williams, et al., "The lyophilization of pharmaceuticals: a literature review." J Parenter Sci Technol. Mar.-Apr. 1984; 38(2): 48-59.
Yamaguchi, et al., "AGER gene polymorphisms and soluble receptor for advanced glycation end product in patients with idiopathic pulmonary fibrosis". Respirology Jul. 2017;22(5):965-971. Epub Feb. 14, 2017.
Yamaguchi, et al., "Reduced endogenous secretory RAGE in blood and bronchoalveolar lavage fluid is associated with poor prognosis in idiopathic pulmonary fibrosis". Respiratory Research 2020; 21, Article No. 145, 8 pages.
Zhang, et al., "Interleukin-6 Regulation of Transforming Growth Factor (TGF)-ß Receptor Compartmentalization and Turnover Enhances TGF-ß1 Signaling". J Biol Chem. Apr. 1, 2005; 280(13): 12239-12245. Epub Jan. 20, 2005.
Zhang, et al., "Pleiotropic functions of glutathione S-transferase P." Adv Cancer Res. 2014; 122: 143-175.
Rafii, et al., "A review of current and novel therapies for idiopathic pulmonary fibrosis". J Thorac Dis. Feb. 2013; 5(1): 48-73.
Ansel et al., Pharmaceutical Dosage Forms and Drug Delivery Systems (6th ED 1995) at pp. 196 and 1456-1457.
Basire, et al., "High urokinase expression contributes to the angiogenic properties of endothelial cells derived from circulating progenitors". Thromb Haemost Apr. 2006; 95(4): 678-688.
Bhandary, et al., "Regulation of lung injury and fibrosis by p53-mediated changes in urokinase and plasminogen activator inhibitor-1". Am J Pathol. Jul. 2013; 183(1): 131-143. Epub May 8, 2013.
Boscher and Nabi, "Caveolin-1: role in cell signaling". Adv Exp Med Biol. 2012; 729: 29-50.
Britain's national health service web page on mesothelioma, [publication date unknown], page last reviewed: Sep. 12, 2022, https://www.nhs.uk/conditions/mesothelioma/, downloaded Jul. 8, 2023, 2 pages.
Chang, et al., "SPARC suppresses apoptosis of idiopathic pulmonary fibrosis fibroblasts through constitutive activation of beta-catenin". J Biol Chem. Mar. 12, 2010; 285(11): 8196-8206. Epub Jan. 8, 2010.
Christiaens, et al., "Tryptophan fluorescence study of the interaction of penetratin peptides with model membranes". Eur J Biochem. Jun. 2002; 269(12): 2918-2926.
Costabel, et al., "Hypersensitivity pneumonitis". Nat Rev Dis Primers. Aug. 6, 2020; 6(1): 65, 19 pages.
Criado, et al., "Pulmonary sarcoidosis: typical and atypical manifestations at high-resolution CT with pathologic correlation". Radiographics. Oct. 2010; 30(6): 1567-1586.
Davis, et al., "Nitric oxide-dependent activation of p53 suppresses bleomycin-induced apoptosis in the lung". J Exp Med. Sep. 18, 2000; 192(6): 857-869.
Degryse, et al., "Repetitive intratracheal bleomycin models several features of idiopathic pulmonary fibrosis". Am J Physiol Lung Cell Mol Physiol. Oct. 2010; 299(4): L442-L452. Epub Jun. 18, 2010.
Dempsey, C.E., "The actions of melittin on membranes". Biochim Biophys Acta. May 7, 1990; 1031(2): 143-161.
Derossi, D., et al., "The third helix of the Antennapedia homeodomain translocates through biological membranes". J Biol Chem. Apr. 8, 1994 ;269(14): 10444-10450.
Dilber, et al., "Intercellular delivery of thymidine kinase prodrug activating enzyme by the herpes simplex virus protein, VP22". Gene Ther. Jan. 1999; 6(1): 12-21.
Dorange, et al., "Marek's disease virus (MDV) homologues of herpes simplex virus type 1 UL49 (VP22) and UL48 (VP16) genes: high-level expression and characterization of MDV-1 VP22 and VP16". J Gen Virol. Sep. 2000; 81(Pt 9): 2219-2230.
Egger, et al., "Administration of bleomycin via the oropharyngeal aspiration route leads to sustained lung fibrosis in mice and rats as

(56) References Cited

OTHER PUBLICATIONS quantified by UTE-MRI and histology". PLoS One. May 7, 2013; 8(5): e63432, _ pages. Print 2013.

Elliott and O'Hare, "Intercellular trafficking and protein delivery by a herpesvirus structural protein". Cell. Jan. 24, 1997; 88(2): 223-233.

Esteve, et al., "Transduction of the scorpion toxin maurocalcine into cells. Evidence that the toxin crosses the plasma membrane". J Biol Chem. Apr. 1, 2005; 280(13): 12833-12839. Epub Jan. 14, 2005.

Extended European Search Report for Application No. EP 19859836.9 dated Jun. 3, 2022, 24 pages.

Extended European Search Report for Application No. EP 20770567.4, dated Oct. 27, 2022, 10 pages.

Extended European Search Report for Application No. EP 21209064.4, dated Aug. 2, 2022, 13 pages.

Fiddler, et al., "Severe Colitis Associated with Pirfenidone Use in Idiopathic Pulmonary Fibrosis". Ann Am Thorac Soc. Aug. 2016; 13(8): 1430-1432.

Frankel and Pabo, "Cellular uptake of the tat protein from human immunodeficiency virus". Cell. Dec. 23, 1988; 55(6): 1189-1193.

Fröhlich and Salar-Behzadi, "Oral inhalation for delivery of proteins and peptides to the lungs". Eur J Pharm Biopharm. Jun. 2021; 163: 198-211. Epub Apr. 11, 2021.

Fridolfsson, et al., "Regulation of intracellular signaling and function by caveolin". FASEB J. Sep. 2014; 28(9): 3823-3831. Epub May 22, 2014.

Futaki, S., et al., "Arginine-rich peptides. An abundant source of membrane-permeable peptides having potential as carriers for intracellular protein delivery". J Biol Chem, 2001. 276(8): p. 5836-5840.

Hoyle, et al., "Emphysematous lesions, inflammation, and fibrosis in the lungs of transgenic mice overexpressing platelet-derived growth factor". Am J Pathol. Jun. 1999; 154(6): 1763-1775.

International Preliminary Examination Report for Application No. PCT/US2020/021980, dated Sep. 23, 2021, 11 pages.

International Preliminary Report on Patentability for Application No. PCT/US2020/021980, dated Aug. 25, 2021, 10 pages.

International Preliminary Report on Patentability for International Application No. PCT/US2019/050332, dated Mar. 9, 2021, 7 pages.

International Preliminary Report on Patentability for International Application No. PCT/US2021/028326 dated Nov. 3, 2022, 7 pages.

International Preliminary Report on Patentability for International Application No. PCT/US2021/037812, dated Dec. 13, 2022, 9 pages.

International Search Report and Written Opinion for Application No. PCTUS2022033929, dated Nov. 7, 2022, 17 pages.

International Search Report and Written Opinion for International Application No. PCT/US2019/050332, dated Dec. 2, 2019, 10 pages.

International Search Report and Written Opinion for International Application No. PCT/US2020/021980, dated Jun. 24, 2020, 13 pages.

International Search Report and Written Opinion for International Application No. PCT/US2022/078482, dated Mar. 3, 2023, 11 pages.

International Search Report and Written Opinion for International Application No. PCT/US2022/017833, dated Aug. 1, 2022.

Invitation to Pay Fee for International Application No. PCT/US2022/017833 dated May 19, 2022, 4 pages.

Invitation to Pay for International Application No. PCT/US2022/033929 dated Aug. 26, 2022, 2 pages.

Invitation to Pay for International Application No. PCT/US2022/078482 dated Jan. 9, 2023, 2 pages.

Izutsu, Ken-ichi, "Stabilization of therapeutic proteins by chemical and physical methods," Therapeutic Proteins, Smales and James, eds, ISBN 1-58829-390-4, 2005.

Joliot, et al., "Antennapedia homeobox peptide regulates neural morphogenesis". Proc Natl Acad Sci U S A. Mar. 1, 1991; 88(5): 1864-1868.

Kobayashi, et al., "Membrane translocation mechanism of the antimicrobial peptide buforin 2". Biochemistry. Dec. 14, 2004; 43(49): 15610-15616.

Konno, et al., "Structure and biological activities of eumenine mastoparan-AF (EMP-AF), a new mast cell degranulating peptide in the venom of the solitary wasp (*Anterhynchium flavomarginatum micado*)". Toxicon. Nov. 2000; 38(11): 1505-1515.

Koptidesova, et al., "Identification and characterization of a cDNA clone derived from the Marek's disease tumour cell line RPL1 encoding a homologue of alpha-transinducing factor (VP16) of HSV-1". Arch Virol. 1995; 140(2): 355-362.

Kummer, et al., "Vascular Signaling in Allogenic Solid Organ Transplantation—The Role of Endothelial Cells." Front Physiol. May 8, 2020; 11: 443, 19 pages. eCollection 2020.

Kunz, "Synthesis of Glycopeptides, Partial Structures of Biological Recognition Components [New Synthetic Methods (67)]†‡". Angewandte Chemie International Ed., vol. 26, Issue 4, Apr. 1987, pp. 294-308.

Lee, et al., "Expression of Caveolin-1 reduces cellular responses to TGF-beta1 through down-regulating the expression of TGF-beta type II receptor gene in NIH3T3 fibroblast cells". Biochem Biophys Res Commun. Jul. 27, 2007; 359(2): 385-390. Epub May 25, 2007.

Li, et al., "Effect of platelet-derived growth factor on the development and persistence of asbestos-induced fibroproliferative lung disease". J Environ Pathol Toxicol Oncol. 2004; 23(4): 253-266.

Lindgren, et al., "Cell-penetrating peptides". Trends Pharmacol Sci. Mar. 2000; 21(3): 99-103.

Lindgren, et al., "Translocation properties of novel cell penetrating transportan and penetratin analogues". Bioconjug Chem. Sep.-Oct. 2000; 11(5): 619-626. d.

Liu, et al., "Fibroblast-specific expression of AC6 enhances beta-adrenergic and prostacyclin signaling and blunts bleomycin-induced pulmonary fibrosis". Am J Physiol Lung Cell Mol Physiol. Jun. 2010; 298(6): L819-L829.

Liu, et al., "p53 Attenuates lipopolysaccharide-induced NF-kappaB activation and acute lung injury". J Immunol. Apr. 15, 2009; 182(8): 5063-5071.

Mace, et a., "HOXA3 induces cell migration in endothelial and epithelial cells promoting angiogenesis and wound repair". J Cell Sci. Jun. 15, 2005; 118(Pt 12): 2567-2577. Epub May 24, 2005.

Malinmvsky, et al., "uPA and PAI-1-Related Signaling Pathways Differ between Primary Breast Cancers and Lymph Node Metastases". Transl Oncol. Apr. 2012; 5(2): 98-104. Epub Apr. 1, 2012.

Maniti, et al., "Distinct behaviour of the homeodomain derived cell penetrating peptide penetratin in interaction with different phospholipids". PLoS One. Dec. 30, 2010; 5(12): e15819, 11 pages.

Markarian, Jennifer, "optimizing Particle Engineering Methods for Inhalation Drug Products", Inhalation Drug Manufacturing, Pharmaceutical Technology (2018); 42(4): 34-46.

Marudamuthu, et al., "Role of the urokinase-fibrinolytic system in epithelial-mesenchymal transition during lung injury". Am J Pathol. Jan. 2015; 185(1): 55-68. Epub Nov. 3, 2014.

Mayo LD, et al., "PTEN protects p53 from Mdm2 and sensitizes cancer cells to chemotherapy". J Biol Chem. Feb. 15, 2002; 277(7): 5484-5489. Epub Nov. 29, 2001.

Meinecke, et al., "Aberrant mural cell recruitment to lymphatic vessels and impaired lymphatic drainage in a murine model of pulmonary fibrosis". Blood. Jun. 14, 2012; 119(24): 5931-5942. Epub Apr. 30, 2012.

Merkel, et al., "Interdependent regulation of p53 and miR-34a in chronic lymphocytic leukemia". Cell Cycle. Jul. 15, 2010; 9(14): 2764-2768. Epub Jul. 3, 2010.

Michel, et al., "Caveolin versus calmodulin." J Biol Chem. Oct. 10, 1997; 272(41): 25907-25912.

Milletti, "Cell-penetrating peptides: classes, origin, and current landscape". Drug Discov Today. Aug. 2012; 17(15-16): 850-860. Epub Mar. 23, 2012.

Miyasato, et al., "Caveolin-1 modulates TGF-β1 signaling in cardiac remodeling." Matrix Biol. Jun. 2011; 30(5-6): 318-329. Epub May 27, 2011.

Morris et al., "A peptide carrier for the delivery of biologically active proteins into mammalian cells". Nat Biotechnol. Dec. 2001; 19(12): 1173-1176.

(56) References Cited

OTHER PUBLICATIONS

Münster, Anna-Marie, et al., "Jet and ultrasonic nebulization of single chain urokinase plasminogen activator (scu-PA)." J Aerosol Med. 2000 Winter; 13(4): 325-333.
Nascimento, et al., "Crotamine mediates gene delivery into cells through the binding to heparan sulfate proteoglycans". J Biol Chem. 2007; 282(29): 21349-21360.
Oparah, et al., "Operative management of penetrating wounds of the chest in civilian practice." J Thorac Cardiovasc Surg. Feb. 1979; 77(2): 162-168.
Padro, et al., "The catalytic domain of endogenous urokinase-type plasminogen activator is required for the mitogenic activity of platelet-derived and basic fibroblast growth factors in human vascular smooth muscle cells". J Cell Sci. May 1, 2002; 115(Pt 9): 1961-1971.
Phelan, et al., "Intercellular delivery of functional p53 by the herpesvirus protein VP22". Nat Biotechnol. May 1998; 16(5): 440-443.
Pooga, et al., "Cell penetration by transportan". FASEB J. Jan. 1998; 12(1): 67-77.
Shetty, et al., "A urokinase receptor mRNA binding protein from rabbit lung fibroblasts and mesothelial cells". Am J Physiol. Jun. 1998; 274(6): L871-L882.
Shetty, et al., "Differential expression of the urokinase receptor in fibroblasts from normal and fibrotic human lungs". Am J Respir Cell Mol Biol. Jul. 1996; 15(1): 78-87.
Shetty, et al., "Regulation of mesothelial cell mitogenesis by antisense oligonucleotides for the urokinase". Antisense Res Dev. 1995 Winter; 5(4): 307-314.
Shetty, et al., "Regulation of plasminogen activator inhibitor-1 expression by tumor suppressor protein p53". J Biol Chem. Jul. 11, 2008; 283(28): 19570-19580. Epub May 9, 2008.
Shetty, et al., "Regulation of urokinase receptor expression by p53: novel role in stabilization of uPAR mRNA". Mol Cell Biol. Aug. 2007; 27(16): 5607-5618. Epub Jun. 4, 2007.
Shetty, et al., "Urokinase expression by tumor suppressor protein p53: a novel role in mRNA turnover". Am J Respir Cell Mol Biol. Sep. 2008; 39(3): 364-372. Epub Apr. 3, 2008.
Shetty, et al., "Urokinase induces expression of its own receptor in Beas2B lung epithelial cells". J Biol Chem. Jul. 6, 2001; 276(27): 24549-24556. Epub May 7, 2001.
Shetty, et al., "Urokinase receptor in human malignant mesothelioma cells: role in tumor cell mitogenesis and proteolysis". Am J Physiol. Jun. 1995; 268(6 Pt 1): L972-L982.
Shetty, et al., "Urokinase receptor mRNA stability involves tyrosine phosphorylation in lung epithelial cells". Am J Respir Cell Mol Biol. Jan. 2004; 30(1): 69-75. Epub Jun. 19, 2003.
Solomon et al., "Scleroderma lung disease". Eur Respir Rev. Mar. 1, 2013; 22(127): 6-19.
Stambohc, et al., "Regulation of PTEN transcription by p53". Mol Cell. Aug. 2001; 8(2): 317-325.
Thornton, et al., "The Arf tumor suppressor regulates platelet-derived growth factor receptor beta signaling: a new view through the eyes of Arf(-/-) mice". Cell Cycle. Oct. 2005; 4(10): 1316-1319. Epub Oct. 17, 2005.
Thorpe, et al., "Comparison of two anti-Thy 1.1-abrin A-chain immunotoxins prepared with different cross-linking agents: antitumor effects, in vivo fate, and tumor cell mutants". J Natl Cancer Inst. Nov. 1987; 79(5): 1101-1112.
Thorpe, et al., "New coupling agents for the synthesis of immunotoxins containing a hindered disulfide bond with improved stability in vivo." Cancer Res. Nov. 15, 1987; 47(22): 5924-5931.
Tiwari et al., "p53 Expression in Lung Fibroblasts: Linkage to Fibrotic Lung Remodeling". C73. Fibroblast Biology (2018); American Thoracic Society International Conference, Abstracts A5789-A5789.
Tkachuk, et al., "Regulation and role of urokinase plasminogen activator in vascular remodelling". Clin Exp Pharmacol Physiol. Sep. 1996; 23(9): 759-765.
Tourkina, et al., "Caveolin-1 signaling in lung fibrosis". Open Rheumatol J. 2012; 6: 116-122. Epub Jun. 15, 2012.
U.S. Appl. No. 18/002,420, filed Dec. 19, 2022.
Van Der Velden et al., "LysoTracker is a marker of differentiated alveolar type II cells". Respir Res. Nov. 11, 2013; 14(1): 123, 7 pages.
Vicellio, "The mesh nebulizer: a recent technical innovation for aerosol delivery." Breath (2006); 2(3): 252-260.
Vives, et al., "A truncated HIV-1 Tat protein basic domain rapidly translocates through the plasma membrane and accumulates in the cell nucleus". J Biol Chem. Jun. 20, 1997; 272(25): 16010-16017.
Volonte, et al., "Caveolin-1 expression is required for the development of pulmonary emphysema through activation of the ATM-p53-p21 pathway". J Biol Chem. Feb. 27, 2009; 284(9): 5462-5466. Epub Dec. 22, 2008.
Wan, et al., "Endostatin, an angiogenesis inhibitor, ameliorates bleomycin induced pulmonary fibrosis in rats." Respir Res. May 20, 2013; 14(1): 56, 13 pages.
Widau, et al., p19Arf represses platelet-derived growth factor receptor β by transcriptional and posttranscriptional mechanisms. Mol Cell Biol. Nov. 2012; 32(21): 4270-4282. Epub Aug. 20, 2012.
Xia , et al., "Pathologic caveolin-1 regulation of PTEN in idiopathic pulmonary fibrosis". Am J Pathol. Jun. 2010; 176(6): 2626-2637. Epub Apr. 15, 2010.
Zhu, et al., "Urokinase receptor mediates lung fibroblast attachment and migration toward provisional matrix proteins through interaction with multiple integrins". Am J Physiol Lung Cell Mol Physiol. Jul. 2009; 297(1): L97-L108. Epub May 1, 2009.

* cited by examiner

SEQUENCE LISTING

```
<160> NUMBER OF SEQ ID NOS: 27

<210> SEQ ID NO 1
<211> LENGTH: 178
<212> TYPE: PRT
<213> ORGANISM: Homo sapiens

<400> SEQUENCE: 1

Met Ser Gly Gly Lys Tyr Val Asp Ser Glu Gly His Leu Tyr Thr Val
1               5                   10                  15

Pro Ile Arg Glu Gln Gly Asn Ile Tyr Lys Pro Asn Asn Lys Ala Met
                20                  25                  30

Ala Asp Glu Leu Ser Glu Lys Gln Val Tyr Asp Ala His Thr Lys Glu
            35                  40                  45

Ile Asp Leu Val Asn Arg Asp Pro Lys His Leu Asn Asp Asp Val Val
        50                  55                  60

Lys Ile Asp Phe Glu Asp Val Ile Ala Glu Pro Glu Gly Thr His Ser
65                  70                  75                  80

Phe Asp Gly Ile Trp Lys Ala Ser Phe Thr Thr Phe Thr Val Thr Lys
                85                  90                  95

Tyr Trp Phe Tyr Arg Leu Leu Ser Ala Leu Phe Gly Ile Pro Met Ala
                100                 105                 110

Leu Ile Trp Gly Ile Tyr Phe Ala Ile Leu Ser Phe Leu His Ile Trp
            115                 120                 125

Ala Val Val Pro Cys Ile Lys Ser Phe Leu Ile Glu Ile Gln Cys Ile
        130                 135                 140

Ser Arg Val Tyr Ser Ile Tyr Val His Thr Val Cys Asp Pro Leu Phe
145                 150                 155                 160

Glu Ala Val Gly Lys Ile Phe Ser Asn Val Arg Ile Asn Leu Gln Lys
                165                 170                 175
```

Glu Ile

```
<210> SEQ ID NO 2
<211> LENGTH: 7
<212> TYPE: PRT
<213> ORGANISM: Artificial sequence
<220> FEATURE:
<223> OTHER INFORMATION: Synthetic amino acid

<400> SEQUENCE: 2

Phe Thr Thr Phe Thr Val Thr
1               5

<210> SEQ ID NO 3
<211> LENGTH: 9
<212> TYPE: PRT
<213> ORGANISM: Artificial sequence
<220> FEATURE:
<223> OTHER INFORMATION: Synthetic amino acid

<400> SEQUENCE: 3

Ala Ser Phe Thr Thr Phe Thr Val Thr
1               5

<210> SEQ ID NO 4
<211> LENGTH: 13
<212> TYPE: PRT
<213> ORGANISM: Artificial sequence
<220> FEATURE:
<223> OTHER INFORMATION: Synthetic amino acid

<400> SEQUENCE: 4

Lys Ala Ser Phe Thr Thr Phe Thr Val Thr Lys Gly Ser
1               5                   10

<210> SEQ ID NO 5
<211> LENGTH: 13
<212> TYPE: PRT
<213> ORGANISM: Artificial sequence
<220> FEATURE:
<223> OTHER INFORMATION: Synthetic amino acid

<400> SEQUENCE: 5

Lys Ala Ser Phe Thr Thr Phe Thr Val Thr Lys Gly Ser
1               5                   10

<210> SEQ ID NO 6
<211> LENGTH: 19
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(2)
<223> OTHER INFORMATION: X = D-Alanine
<220> FEATURE:
<221> NAME/KEY: MISC_FEATURE
<222> LOCATION: (18)..(19)
<223> OTHER INFORMATION: X = D-Alanine

<400> SEQUENCE: 6

Xaa Xaa Glu Gly Lys Ala Ser Phe Thr Thr Phe Thr Val Thr Lys Gly
1               5                   10                  15

Ser Xaa Xaa

<210> SEQ ID NO 7
```

```
<211> LENGTH: 19
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(2)
<223> OTHER INFORMATION: X = D-Alanine
<220> FEATURE:
<221> NAME/KEY: MISC_FEATURE
<222> LOCATION: (18)..(19)
<223> OTHER INFORMATION: X = D-Alanine
<220> FEATURE:
<221> NAME/KEY: MISC_FEATURE
<222> LOCATION: (19)..(19)
<223> OTHER INFORMATION: NH2 functional group present

<400> SEQUENCE: 7

Xaa Xaa Glu Gly Lys Ala Ser Phe Thr Thr Phe Thr Val Thr Lys Gly
1               5                   10                  15

Ser Xaa Xaa

<210> SEQ ID NO 8
<211> LENGTH: 19
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
<220> FEATURE:
<221> NAME/KEY: MISC_FEATURE
<222> LOCATION: (1)..(2)
<223> OTHER INFORMATION: X = D-Alanine
<220> FEATURE:
<221> NAME/KEY: MISC_FEATURE
<222> LOCATION: (18)..(19)
<223> OTHER INFORMATION: X = D-Alanine
<220> FEATURE:
<221> NAME/KEY: MISC_FEATURE
<222> LOCATION: (19)..(19)
<223> OTHER INFORMATION: NH2 functional group present

<400> SEQUENCE: 8

Xaa Xaa Glu Gly Lys Ala Ser Phe Thr Thr Phe Thr Val Thr Lys Gly
1               5                   10                  15

Ser Xaa Xaa

<210> SEQ ID NO 9
<211> LENGTH: 12
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: X = Ornithine
<220> FEATURE:
<221> NAME/KEY: MISC_FEATURE
<222> LOCATION: (11)..(11)
<223> OTHER INFORMATION: X = Ornithine

<400> SEQUENCE: 9

Xaa Ala Ser Phe Thr Thr Phe Thr Val Thr Xaa Ser
1               5                   10

<210> SEQ ID NO 10
```

```
<211> LENGTH: 12
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: X = Ornithine
<220> FEATURE:
<221> NAME/KEY: MISC_FEATURE
<222> LOCATION: (11)..(11)
<223> OTHER INFORMATION: X = Ornithine
<220> FEATURE:
<221> NAME/KEY: MISC_FEATURE
<222> LOCATION: (12)..(12)
<223> OTHER INFORMATION: NH2 functional group present

<400> SEQUENCE: 10

Xaa Ala Ser Phe Thr Thr Phe Thr Val Thr Xaa Ser
1               5                   10

<210> SEQ ID NO 11
<211> LENGTH: 7
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (7)..(7)
<223> OTHER INFORMATION: NH2 functional group present

<400> SEQUENCE: 11

Phe Thr Thr Phe Thr Val Thr
1               5

<210> SEQ ID NO 12
<211> LENGTH: 8
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (8)..(8)
<223> OTHER INFORMATION: NH2 functional group present

<400> SEQUENCE: 12

Phe Thr Thr Phe Thr Val Thr Lys
1               5

<210> SEQ ID NO 13
<211> LENGTH: 11
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (11)..(11)
<223> OTHER INFORMATION: NH2 functional group present

<400> SEQUENCE: 13

Lys Ala Ser Phe Thr Thr Phe Thr Val Thr Lys
1               5                   10

<210> SEQ ID NO 14
<211> LENGTH: 11
<212> TYPE: PRT
<213> ORGANISM: Artificial sequence
```

-continued

```
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
<220> FEATURE:
<221> NAME/KEY: MISC_FEATURE
<222> LOCATION: (11)..(11)
<223> OTHER INFORMATION: NH2 functional group present

<400> SEQUENCE: 14

Lys Ala Ser Phe Thr Thr Phe Thr Val Thr Lys
1               5                   10

<210> SEQ ID NO 15
<211> LENGTH: 11
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: X = Ornithine
<220> FEATURE:
<221> NAME/KEY: MISC_FEATURE
<222> LOCATION: (11)..(11)
<223> OTHER INFORMATION: NH2 functional group present

<400> SEQUENCE: 15

Xaa Ala Ser Phe Thr Thr Phe Thr Val Thr Lys
1               5                   10

<210> SEQ ID NO 16
<211> LENGTH: 11
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
<220> FEATURE:
<221> NAME/KEY: MISC_FEATURE
<222> LOCATION: (1)..(1)
<223> OTHER INFORMATION: X = Ornithine
<220> FEATURE:
<221> NAME/KEY: MISC_FEATURE
<222> LOCATION: (11)..(11)
<223> OTHER INFORMATION: NH2 functional group present

<400> SEQUENCE: 16

Xaa Ala Ser Phe Thr Thr Phe Thr Val Thr Lys
1               5                   10

<210> SEQ ID NO 17
<211> LENGTH: 13
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
<220> FEATURE:
<221> NAME/KEY: MISC_FEATURE
<222> LOCATION: (13)..(13)
<223> OTHER INFORMATION: NH2 functional group present

<400> SEQUENCE: 17
```

Lys Ala Ser Phe Thr Thr Phe Thr Val Thr Lys Gly Ser
1               5                   10

<210> SEQ ID NO 18
<211> LENGTH: 14
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (14)..(14)
<223> OTHER INFORMATION: NH2 functional group present

<400> SEQUENCE: 18

Asp Ser Gly Lys Ala Ser Phe Thr Thr Phe Thr Val Thr Lys
1               5                   10

<210> SEQ ID NO 19
<211> LENGTH: 14
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
<220> FEATURE:
<221> NAME/KEY: MISC_FEATURE
<222> LOCATION: (14)..(14)
<223> OTHER INFORMATION: NH2 functional group present

<400> SEQUENCE: 19

Asp Ser Gly Lys Ala Ser Phe Thr Thr Phe Thr Val Thr Lys
1               5                   10

<210> SEQ ID NO 20
<211> LENGTH: 12
<212> TYPE: PRT
<213> ORGANISM: Artificial sequence
<220> FEATURE:
<223> OTHER INFORMATION: Synthetic amino acid
<220> FEATURE:
<221> NAME/KEY: MISC_FEATURE
<222> LOCATION: (1)..(1)
<223> OTHER INFORMATION: Acetyl group present
<220> FEATURE:
<221> NAME/KEY: MISC_FEATURE
<222> LOCATION: (1)..(1)
<223> OTHER INFORMATION: X = Ornithine
<220> FEATURE:
<221> NAME/KEY: MISC_FEATURE
<222> LOCATION: (11)..(11)
<223> OTHER INFORMATION: X = Ornithine
<220> FEATURE:
<221> NAME/KEY: MISC_FEATURE
<222> LOCATION: (12)..(12)
<223> OTHER INFORMATION: NH2 functional group present

<400> SEQUENCE: 20

Xaa Ala Ser Phe Thr Thr Phe Thr Val Thr Xaa Ser
1               5                   10

<210> SEQ ID NO 21
<211> LENGTH: 13
<212> TYPE: PRT
<213> ORGANISM: Artificial sequence
<220> FEATURE:
<223> OTHER INFORMATION: Synthetic amino acid

```
<400> SEQUENCE: 21

Gly Arg Lys Lys Arg Arg Gln Arg Arg Pro Pro Gln
1               5                   10

<210> SEQ ID NO 22
<211> LENGTH: 16
<212> TYPE: PRT
<213> ORGANISM: Artificial sequence
<220> FEATURE:
<223> OTHER INFORMATION: Synthetic amino acid

<400> SEQUENCE: 22

Arg Gln Ile Lys Ile Trp Phe Gln Asn Arg Arg Met Lys Trp Lys Lys
1               5                   10                  15

<210> SEQ ID NO 23
<211> LENGTH: 26
<212> TYPE: PRT
<213> ORGANISM: Artificial sequence
<220> FEATURE:
<223> OTHER INFORMATION: Synthetic amino acid

<400> SEQUENCE: 23

Gly Ile Gly Ala Val Leu Lys Val Leu Thr Thr Gly Leu Pro Ala Leu
1               5                   10                  15

Ile Ser Trp Ile Lys Arg Lys Arg Gln Gln
            20                  25

<210> SEQ ID NO 24
<211> LENGTH: 10
<212> TYPE: PRT
<213> ORGANISM: Artificial sequence
<220> FEATURE:
<223> OTHER INFORMATION: Synthetic amino acid

<400> SEQUENCE: 24

Thr Lys Ile Glu Ser Leu Lys Glu His Gly
1               5                   10

<210> SEQ ID NO 25
<211> LENGTH: 10
<212> TYPE: PRT
<213> ORGANISM: Artificial sequence
<220> FEATURE:
<223> OTHER INFORMATION: Synthetic amino acid

<400> SEQUENCE: 25

Thr Gln Ile Glu Asn Leu Lys Glu Lys Gly
1               5                   10

<210> SEQ ID NO 26
<211> LENGTH: 26
<212> TYPE: PRT
<213> ORGANISM: Artificial sequence
<220> FEATURE:
<223> OTHER INFORMATION: Synthetic amino acid

<400> SEQUENCE: 26

Ala Ala Leu Glu Ala Leu Ala Glu Ala Leu Glu Ala Leu Glu Ala
1               5                   10                  15

Leu Glu Ala Leu Ala Glu Ala Ala Ala Ala
            20                  25

<210> SEQ ID NO 27
<211> LENGTH: 25
```

```
<212> TYPE: PRT
<213> ORGANISM: Artificial sequence
<220> FEATURE:
<223> OTHER INFORMATION: Synthetic amino acid

<400> SEQUENCE: 27

Gly Leu Phe Glu Ala Ile Glu Gly Phe Ile Glu Asn Gly Trp Glu Gly
1               5                   10                  15

Met Ile Glu Gly Trp Tyr Gly Cys Gly
                20              25
```

MODIFIED PEPTIDE FRAGMENTS OF CAV-1 PROTEIN AND THE USE THEREOF IN THE TREATMENT OF FIBROSIS

This application is a U.S. National Phase application, filed under 35 U.S.C. § 371, of International Application No. PCT/US2019/050332, filed on Sep. 10, 2019, which claims the benefit of U.S. Provisional Patent Application No. 62/728,997, filed Sep. 10, 2018, the entirety of the disclosure of each of which is incorporated herein by reference.

REFERENCE TO AN ELECTRONIC SEQUENCE LISTING

The contents of the electronic sequence listing (LUTX_009_01US_SeqList_ST25; Size: 10,650 bytes; and Date of Creation: Mar. 9, 2021) are herein incorporated by reference in its entirety.

BACKGROUND OF THE INVENTION

1. Field of the Invention

The present invention relates generally to the fields of molecular biology and medicine. More particularly, it concerns compositions and methods for the delivery of therapeutic polypeptide compositions to subjects, such as by delivery to the respiratory system.

2. Description of Related Art

During lung injury, p53 expression increases, inducing plasminogen activator inhibitor-1 (PAI-1) while inhibiting expression of urokinase-type plasminogen activator (uPA) and its receptor (uPAR), resulting in apoptosis of lung epithelial cells (LECs). The mechanism of injury involves cell surface signaling interactions between uPA, uPAR, caveolin-1 ("Cav-1") and β1-integrin (Shetty et al., 2005). Compositions that modulate these interactions could be used in methods for inhibiting apoptosis of injured or damaged lung epithelial cells and for treating acute lung injury and consequent pulmonary fibrosis. Thus, there is a need for polypeptides that could be used to prevent or treat lung injury and, in particular, formulations and methods for therapeutic delivery of such polypeptides.

SUMMARY OF THE INVENTION

In accordance with the present disclosure, there is provided a peptide comprising the amino acid sequence of SEQ ID NO: 2, wherein the peptide comprises at least one N- or C-terminal addition. The N- or C-terminal additions may be standard amino acids, non-standard amino acids, or chemical modifications. There are provided peptide multimers of the peptide of the disclosure. Also provided is a pharmaceutical composition of the peptide. Peptides of the present disclosure may be used to treat lung injuries, infections or diseases. In further aspects, peptides of the embodiments can be used to treat fibrotic conditions, e.g., organ fibrosis, or inflammation.

In some embodiments, the present disclosure provides a peptide comprising the amino acid sequence ASFTTFTVT (SEQ ID NO: 3), wherein the peptide comprises at least one N- or C-terminal addition lacking identity to SEQ ID NO: 1. In some aspects, the peptide comprises at least one amino acid added to the N-terminus. In some aspects, the peptide comprises at least one amino acid added to the C-terminus. In some aspects, the peptide comprises at least one amino acid added to the N-terminus and the C-terminus. In some aspects, the peptide maintains the biological activity of caveolin-1 (Cav-1). In further aspects, a peptide of the embodiments can be comprise one or more deuterated residues.

In some aspects, the peptide comprises L-amino acids. In some aspects, the peptide comprises D-amino acids. In some aspects, the peptide comprises both L- and D-amino acids.

In some aspects, the peptide comprises at least one non-standard amino acid. In some aspects, the peptide comprises 2 or more non-standard amino acids. In some aspects, the peptide comprises 4 or more non-standard amino acids. In some aspects, the non-standard amino acid is ornithine. In some aspects, the non-standard amino acid is D-alanine.

In some aspects, the peptide comprises N- or C-terminal modifications. In some aspects, the peptide comprises a N-terminal modification. In some aspects, the peptide comprises a C-terminal modification. In some aspects, the peptide comprises a N- and C-terminal modification. In some aspects, the N-terminal modification is acylation. In some aspects, the C-terminal modification is amidation.

In some aspects, the peptide comprises the amino acid sequence KASFTTFTVTKGS (SEQ ID NO: 4). In some aspects, the peptide comprises the amino acid sequence aaEGKASFTTFTVTKGSaa (SEQ ID NO: 6). In other aspects, the peptide comprises the amino acid sequence OASFTTFTVTOS (SEQ ID NO: 9). In other aspects, the peptide comprises the amino acid sequence aaE-GKASFTTFTVTKGSaa-NH2 (SEQ ID NO: 7). In still other aspects, the peptide comprises the amino acid sequence Ac-aaEGKASFTTFTVTKGSaa-NH2 (SEQ ID NO: 8). In other aspects, the peptide comprises the amino acid sequence OASFTTFTVTOS-NH2 (SEQ ID NO: 10).

In some aspects, the peptide further comprises a cell-penetrating peptide (CPP). In some embodiments the CPP comprises an amino acid sequence selected from the group comprising: GRKKRRQRRRPPQ (SEQ ID NO: 21), RQIKIWFQNRRMKWKK (SEQ ID NO:22), and GIGAVLKVLTTGLPALISWIKRKRQQ (SEQ ID NO:23).

In some embodiments, the disclosure provides a peptide multimer comprising at least two peptides as disclosed herein. In some aspects, a first peptide of the at least two peptides is essentially identical to a second peptide of the at least two peptides. In other aspects, a first peptide of the at least two peptides is not identical to a second peptide of the at least two peptides.

In some embodiments, the disclosure provides a composition comprising peptides disclosed herein. In some aspects, the peptides are substantially pure. In some aspects, the peptides are at least 95% pure, at least 96% pure, at least 97% pure, at least 98% pure, or at least 99% pure.

In some embodiments, the disclosure provides a pharmaceutical composition comprising the peptide a peptide as disclosed herein and a pharmaceutically acceptable carrier. In some aspects, the pharmaceutical composition is formulated for oral, intravenous, intraarticular, parenteral, enteral, topical, subcutaneous, intramuscular, buccal, sublingual, rectal, intravaginal, intrapenile, intraocular, epidural, intracranial, or inhalational administration. In some aspects, the pharmaceutical composition is formulated for lung instillation. In some aspects, the pharmaceutical composition is formulated as a nebulized solution.

In some embodiments, the disclosure provides a polynucleotide comprising a nucleic acid sequence encoding the peptide as described herein.

In certain aspects, a peptide composition of the embodiments can be used in a method of treating or preventing disease in subject. In some aspects the disease is a fibrotic or inflammatory disease. For example, the fibrotic disease can be organ fibrotic disease, can be kidney, liver, lung or heart fibrosis. In some aspects, the inflammatory disease is an inflammatory eye disease. Compositions of the embodiments can be administered systemically or locally (e.g., at the site of diseased tissues).

In some embodiments, the disclosure provides a method of treating or preventing acute lung injury, lung infection or lung disease in a subject comprising administering to the subject an effective amount of the peptide as described herein. In some aspects, the subject has pulmonary inflammation. In some aspects, the subject is undergoing chemotherapy or radiation therapy. In some aspects, the subject has an acute lung injury or infection. In some aspects, the subject has a chemical-induced lung injury. In some aspects, the subject has plastic bronchitis, chronic obstructive pulmonary disease, bronchitis, bronchiolitis, bronchiolitis obliterans, asthma, acute respiratory distress syndrome (ARDS) or inhalational smoke induced acute lung injury (ISALI). In some aspects, the lung disease is a fibrotic condition of the lungs. In some aspects, the lung disease is interstitial lung disease. In some aspects, the lung disease is Idiopathic Pulmonary Fibrosis (IPF) or lung scarring. In some aspects, the administering comprises nebulizing a solution comprising the peptide. In some aspects, the method further comprises administering at least one additional anti-fibrotic therapeutic. In some aspects, the at least one additional anti-fibrotic is NSAID, steroid, DMARD, immunosuppressive, biologic response modulators, or bronchodilator. In some aspects, the subject is a human.

It is contemplated that any method or composition described herein can be implemented with respect to any other method or composition described herein. Other objects, features and advantages of the present disclosure will become apparent from the following detailed description. It should be understood, however, that the detailed description and the specific examples, while indicating specific embodiments of the disclosure, are given by way of illustration only, since various changes and modifications within the spirit and scope of the disclosure will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

Figure 1:
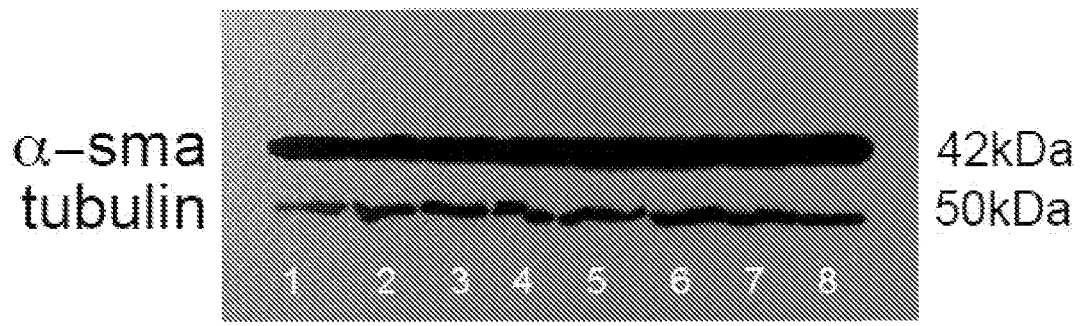
FIG. 1: Western blot of SMA and tubulin idiopathic pulmonary fibrosis cells treated with Cav-1 peptides. IPF cells were treated with: 1: Untreated, 2:10 µM LTI-03, 3: 90 µM LTI-03, 4: 10 µM APi2350, 5: 10 µM APi2354, 6: 10 µM APi2355, 7: 10 µM APi2356, and 8: DMSO, and SMA and tubulin expression was evaluated by western blot.

The present disclosure overcomes challenges associated with current technologies by providing modified caveolin-1 (Cav-1) peptides and the use thereof for disease treatment and prevention, particularly lung fibrosis. In some aspects, pharmaceutical formulations of the modified Cav-1 peptides are provided. For example, in some aspects, the peptide is formulated for delivery to the respiratory system. For instance, peptides can be prepared for administration to a subject's airway by formulation in an aqueous solution and nebulizing the solution using a nebulizer. In other aspects, peptides can be formulated for injection. Also provided herein is a method of treating lung injuries and diseases, by administering to the subject (e.g., via the airway) a therapeutically effective amount of a modified Cav-1 peptide.

I. DEFINITIONS

As used herein, "essentially free," in terms of a specified component, is used herein to mean that none of the specified component has been purposefully formulated into a composition and/or is present only as a contaminant or in trace amounts. The total amount of the specified component resulting from any unintended contamination of a composition is therefore well below 0.01%. Most preferred is a composition in which no amount of the specified component can be detected with standard analytical methods.

As used herein the specification, "a" or "an" may mean one or more. As used herein in the claim(s), when used in conjunction with the word "comprising," the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

The term "peptide" as used herein typically refers to a sequence of amino acids made up of a single chain of amino acids joined by peptide bonds. Generally, peptides contain at least two amino acid residues and are less than about 50 amino acids in length, unless otherwise defined.

A "biologically active" caveolin-1 (Cav-1) peptide refers to a peptide that increases p53 protein levels, reduces urokinase plasminogen activator (uPA) and uPA receptor (uPAR), and/or increases plasminogen activator inhibitor-1 (PAI-1) expression in cells, such as fibrotic lung fibroblasts. In some aspects, the biologically active peptide has at least 20% of the biological or biochemical activity of native Cav-1 polypeptide of SEQ ID NO: 1 (e.g., as measured by an in vitro or an in vivo assay). In some aspects, the biological active peptide has an increase biological or biochemical activity as compared to the native Cav-1 polypeptide.

The term "identity" or "homology" shall be construed to mean the percentage of amino acid residues in the candidate sequence that are identical with the residue of a corresponding sequence to which it is compared, after aligning the sequences and introducing gaps, if necessary to achieve the maximum percent identity for the entire sequence, and not considering any conservative substitutions as part of the sequence identity. Neither N- or C-terminal extensions nor insertions shall be construed as reducing identity or homology. Methods and computer programs for the alignment are well known in the art. Sequence identity may be measured using sequence analysis software.

The term "polypeptide" or "protein" is used in its broadest sense to refer to a compound of two or more subunit amino acids, amino acid analogs, or peptidomimetics. The subunits may be linked by peptide bonds. In another embodiment, the subunit may be linked by other bonds, e.g. ester, ether, etc.

As used herein the term "amino acid" refers to either natural and/or unnatural or synthetic amino acids, including glycine and both the D or L optical isomers, and amino acid analogs and peptidomimetics. The term "peptidomimetic" or "peptide mimic" means that a peptide according to the invention is modified in such a way that it includes at least one non-peptidic bond such as, for example, urea bond, carbamate bond, sulfonamide bond, hydrazine bond, or any other covalent bond. A peptide of three or more amino acids is commonly called an oligopeptide if the peptide chain is short. If the peptide chain is long, the peptide is commonly called a polypeptide or a protein.

The terms "subject" and "individual" and "patient" are used interchangeably herein, and refer to an animal, for example a human or non-human animal (e.g., a mammal), to whom treatment, including prophylactic treatment, with a pharmaceutical composition as disclosed herein, is provided. The term "subject" as used herein refers to human and non-human animals. The term "non-human animals" includes all vertebrates, e.g., mammals, such as non-human primates, (particularly higher primates), sheep, dogs, rodents (e.g. mouse or rat), guinea pigs, goats, pigs, cats, rabbits, cows, and non-mammals such as chickens, amphibians, reptiles etc. In one embodiment, the subject is human. In another embodiment, the subject is an experimental animal or animal substitute as a disease model. Non-human mammals include mammals such as non-human primates, (particularly higher primates), sheep, dogs, rodents (e.g. mouse or rat), guinea pigs, goats, pigs, cats, rabbits and cows. In some aspects, the non-human animal is a companion animal such as a dog or a cat.

"Treating" a disease or condition in a subject or "treating" a patient having a disease or condition refers to subjecting the individual to a pharmaceutical treatment, e.g., the administration of a drug, such that at least one symptom of the disease or condition is decreased or stabilized. Typically, when the peptide is administered therapeutically as a treatment, it is administered to a subject who presents with one or more symptoms of lung injury or lung fibrosis.

By "isolated" it is meant that the polypeptide has been separated from any natural environment, such as a body fluid, e.g., blood, and separated from the components that naturally accompany the peptide.

By isolated and "substantially pure" is meant a polypeptide that has been separated and purified to at least some degree from the components that naturally accompany it. Typically, a polypeptide is substantially pure when it is at least about 60%, or at least about 70%, at least about 80%, at least about 90%, at least about 95%, or even at least about 99%, by weight, free from the proteins and naturally-occurring organic molecules with which it is naturally associated. For example, a substantially pure polypeptide may be obtained by extraction from a natural source, by expression of a recombinant nucleic acid in a cell that does not normally express that protein, or by chemical synthesis.

The term "variant" as used herein refers to a polypeptide or nucleic acid that differs from the polypeptide or nucleic acid by one or more amino acid or nucleic acid deletions, additions, substitutions or side-chain modifications, yet retains one or more specific functions or biological activities of the naturally occurring molecule. Amino acid substitutions include alterations in which an amino acid is replaced with a different naturally-occurring or a non-conventional amino acid residue. Such substitutions may be classified as "conservative", in which case an amino acid residue contained in a polypeptide is replaced with another naturally occurring amino acid of similar character either in relation to polarity, side chain functionality or size. Such conservative substitutions are well known in the art. Substitutions encompassed by the present invention may also be "non-conservative", in which an amino acid residue which is present in a peptide is substituted with an amino acid having different properties, such as naturally-occurring amino acid from a different group (e.g., substituting a charged or hydrophobic amino; acid with alanine), or alternatively, in which a naturally-occurring amino acid is substituted with a non-conventional amino acid. In some embodiments, amino acid substitutions are conservative. Also encompassed within the term variant when used with reference to a polynucleotide or polypeptide, refers to a polynucleotide or polypeptide that can vary in primary, secondary, or tertiary structure, as compared to a reference polynucleotide or polypeptide, respectively (e.g., as compared to a wild-type polynucleotide or polypeptide).

The term "insertions" or "deletions" are typically in the range of about 1 to 5 amino acids. The variation allowed can be experimentally determined by producing the peptide synthetically while systematically making insertions, deletions, or substitutions of nucleotides in the sequence using recombinant DNA techniques.

The term "substitution" when referring to a peptide, refers to a change in an amino acid for a different entity, for example another amino acid or amino-acid moiety. Substitutions can be conservative or non-conservative substitutions.

An "analog" of a molecule such as a peptide refers to a molecule similar in function to either the entire molecule or to a fragment thereof. The term "analog" is also intended to include allelic species and induced variants. Analogs typically differ from naturally occurring peptides at one or a few positions, often by virtue of conservative substitutions. Analogs typically exhibit at least 80 or 90% sequence identity with natural peptides. Some analogs also include unnatural amino acids or modifications of N or C terminal amino acids. Examples of unnatural amino acids are, for example but not limited to; disubstituted amino acids, N-alkyl amino acids, lactic acid, 4-hydroxyproline, γ-carboxyglutamate, ε-N,N,N-trimethyllysine, ε-N-acetyllysine, O-phosphoserine, N-acetylserine, N-formylmethionine, 3-methylhistidine, 5-hydroxylysine, σ-N-methylarginine. Fragments and analogs can be screened for prophylactic or therapeutic efficacy in transgenic animal models as described below.

By "covalently bonded" is meant joined either directly or indirectly (e.g., through a linker) by a covalent chemical bond. In some aspects of all the embodiments of the invention, the fusion peptides are covalently bonded.

The term "fusion protein" as used herein refers to a recombinant protein of two or more proteins. Fusion proteins can be produced, for example, by a nucleic acid sequence encoding one protein is joined to the nucleic acid encoding another protein such that they constitute a single open-reading frame that can be translated in the cells into a single polypeptide harboring all the intended proteins. The order of arrangement of the proteins can vary. Fusion proteins can include an epitope tag or a half-life extender. Epitope tags include biotin, FLAG tag, c-myc, hemaglutinin, His6, digoxigenin, FITC, Cy3, Cy5, green fluorescent protein, V5 epitope tags, GST, β-galactosidase, AU1, AU5, and avidin. Half-life extenders include Fc domain and serum albumin.

The term "airway" refers herein to any portion of the respiratory tract including the upper respiratory tract, the respiratory airway, and the lungs. The upper respiratory tract includes the nose and nasal passages, mouth, and throat. The respiratory airway includes the larynx, trachea, bronchi and bronchioles. The lungs include the respiratory bronchioles, alveolar ducts, alveolar sacs and alveoli.

The terms "inhalational smoke induced acute lung injury" and "ISALI" are used interchangeably herein and refer to a form of acute lung injury (ALI) caused by smoke inhalation. ALI is also referred to as "mild Acute Respiratory Distress Syndrome; ARDS." ARDS can be defined by finding one or more of the following conditions in a subject: 1) bilateral pulmonary infiltrates on chest x-ray, 2) when measured by right heart catheterization as clinically indicated, pulmonary capillary wedge pressure <18 mmHg (2.4 kPa), and 3) $PaO_2/FiO_2$<300 mmHg (40 kPa). In some embodiments, treatment of ISALI includes treatment of one or more of the following conditions: reduced oxygenation, airway obstruction (including a severe airway obstruction), fibrinous airway casts or debris, and alveolar fibrin deposition.

The terms "nebulizing," "nebulized" and other grammatical variations, refer herein to the process of converting a liquid into small aerosol droplets. In some embodiments, the aerosol droplets have a median diameter of approximately 2-10 µm. In some embodiments, the aerosol droplets have a median diameter of approximately 2-4 µm.

II. CAVEOLIN-1 PEPTIDES

Embodiments of the present disclosure provide peptide variants of the caveolin-1 (Cav-1) protein. The Caveolin-1 (Cav-1) scaffolding domain or polypeptide interferes with Cav-1 interaction with Src kinases mimics the combined effect of uPA and anti-β1-integrin antibody. Native human Cav-1 has a length of 178 amino acids and a molecular weight of 22 kDa. The amino acid sequence of Cav-1 is shown below (SEQ ID NO:1).

```
  1   MSGGKYVDSE GHLYTVPIRE QGNIYKPNNK AMADELSEKQ VYDAHTKEID LVNRDPKHLN

61   DDVVKIDFED VIAEPEGTHS FDGIWKASFT TFTVTKYWFY RLLSALFGIP MALIWGIYFA

121   ILSFLHIWAV VPCIKSFLIE IQCISRVYSI YVHTVCDPLF EAVGKIFSNV RINLQKEI
```

In some aspects, the peptide is a scaffolding domain peptide which comprises an amino acid sequence at least about 40%, 50%, 60%, 70%, 80%, 85%, 80%, 85%, 90%, 91%, 92%, 93%, 94%, 95%, 96%, 97%, 98% or 99% identical to SEQ ID NO: 2, FTTFTVT. The peptide may comprise 1, 2, 3, 4 or more amino acid substitutions, deletions, or insertions relative to the sequence of SEQ ID NO:1, such as to derive a polypeptide of 3, 4, 5, 6, 7, 8, 9, 10, 11, 12, 13, 14, 15, 16, 17, 18, or 19 residues. In particular aspects, the peptides are truncations of the native Cav-1 polypeptide, such as the exemplary polypeptides shown in Table 1.

TABLE 1

Exemplary Cav-1 peptides.

| Sequence | ID |
| --- | --- |
| ASFTTFTVT | SEQ ID NO: 3 |
| KASFTTFTVTKGS | SEQ ID NO: 4 |
| KASFTTFTVTKGS-NH2 | SEQ ID NO: 5 |
| aaEGKASFTTFTVTKGSaa | SEQ ID NO: 6 |
| aaEGKASFTTFTVTKGSaa-NH2 | SEQ ID NO: 7 |
| Ac-aaEGKASFTTFTVTKGSaa-NH2 | SEQ ID NO: 8 |
| OASFTTFTVTOS | SEQ ID NO: 9 |
| OASFTTFTVTOS-NH2 | SEQ ID NO: 10 |
| FTTFTVT-NH2 | SEQ ID NO: 11 |
| FTTFTVTK-NH2 | SEQ ID NO: 12 |
| KASFTTFTVTK-NH2 | SEQ ID NO: 13 |

TABLE 1-continued

Exemplary Cav-1 peptides.

| Sequence | ID |
| --- | --- |
| Ac-KASFTTFTVTK-NH2 | SEQ ID NO: 14 |
| OASFTTFTVTK-NH2 | SEQ ID NO: 15 |
| Ac-OASFTTFTVTK-NH2 | SEQ ID NO: 16 |
| Ac-KASFTTFTVTKGS-NH2 | SEQ ID NO: 17 |
| DSGKASFTTFTVTK-NH2 | SEQ ID NO: 18 |
| Ac-DSGKASFTTFTVTK-NH2 | SEQ ID NO: 19 |
| Ac-OASFTTFTVTOS-NH2 | SEQ ID NO: 20 |

(a = D-Alanine, O = Ornithine)

The peptides provided in the present disclosure are biologically active derivatives which have the activity of the native CAV-1 polypeptide in in vitro or in vivo assays of binding or of biological activity. In particular aspects, the peptide inhibits or prevents apoptosis of LECs induced by BLM in vitro or in vivo with activity at least about 20% of the activity of the native CAV-1 polypeptide, or at least about 30%, 40%, 50%, 60%, 65%, 70%, 75%, 80%, 85%, 90%, about 95%, 97%, 99%, and any range derivable therein, such as, for example, from about 70% to about 80%, and more preferably from about 81% to about 90%; or even more preferably, from about 91% to about 99%. The peptide may have 100% or even greater activity than the native CAV-1 polypeptide. Assays for testing biological activity, e.g., anti-fibrotic activity, the ability to affect expression of uPA, uPAR and PAI-1 mRNAs, or inhibit proliferation of lung fibroblasts, are well-known in the art.

The peptides of the present disclosure are peptides of the native Cav-1 polypeptide or modified versions thereof. The peptides can be synthetic, recombinant, or chemically modified peptides isolated or generated using methods well known in the art. Modifications can be made to amino acids on the N-terminus, C-terminus, or internally. N-terminal modifications may be, for example but not limited to, acylation, acetylation, or C-terminal amidation. Peptides can include conservative or non-conservative amino acid changes, as described below. Polynucleotide changes can result in amino acid substitutions, additions, deletions, fusions and truncations in the polypeptide encoded by the reference sequence. Peptides can also include insertions, deletions or substitutions of amino acids, including insertions and substitutions of amino acids (and other molecules) that do not normally occur in the peptide sequence that is the basis of the modified variant, for example but not limited to insertion L-amino acids, or non-standard amino acids such as ornithine, which do not normally occur in human proteins. The term conservative substitution, when describing a peptide, refers to a change in the amino acid composition of the peptide that does not substantially alter the peptide's activity. For example, a conservative substitution refers to substituting an amino acid residue for a different amino acid residue that has similar chemical properties. Conservative amino acid substitutions include replacement of a leucine with an isoleucine or valine, an aspartate with a glutamate, or a threonine with a serine.

Conservative amino acid substitutions result from replacing one amino acid with another having similar structural and/or chemical properties, such as the replacement of a leucine with an isoleucine or valine, an aspartate with a glutamate, or a threonine with a serine. Thus, a conservative substitution of a particular amino acid sequence refers to substitution of those amino acids that are not critical for polypeptide activity or substitution of amino acids with other amino acids having similar properties (e.g., acidic, basic, positively or negatively charged, polar or non-polar, etc.) such that the substitution of even critical amino acids does not reduce the activity of the peptide. Conservative substitution tables providing functionally similar amino acids are well known in the art. For example, the following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W. H. Freeman and Company (1984), incorporated by reference in its entirety.) In some embodiments, individual substitutions, deletions or additions that alter, add or delete a single amino acid or a small percentage of amino acids can also be considered conservative substitutions if the change does not reduce the activity of the peptide. Insertions or deletions are typically in the range of about 1 to 5 amino acids. The choice of conservative amino acids may be selected based on the location of the amino acid to be substituted in the peptide, for example if the amino acid is on the exterior of the peptide and expose to solvents, or on the interior and not exposed to solvents.

In alternative embodiments, one can select the amino acid which will substitute an existing amino acid based on the location of the existing amino acid, i.e. its exposure to solvents (i.e. if the amino acid is exposed to solvents or is present on the outer surface of the peptide or polypeptide as compared to internally localized amino acids not exposed to solvents). Selection of such conservative amino acid substitutions are well known in the art, for example as disclosed in Dordo et al, *J. Mol Biol*, 1999, 217, 721-739 and Taylor et al, *J. Theor. Biol.* 119(1986); 205-218 and S. French and B. Robson, *J. Mol. Evol.* 19(1983)171. Accordingly, one can select conservative amino acid substitutions suitable for amino acids on the exterior of a protein or peptide (i.e. amino acids exposed to a solvent), for example, but not limited to, the following substitutions can be used: substitution of Y with F, T with S or K, P with A, E with D or Q, N with D or G, R with K, G with N or A, T with S or K, D with N or E, I with L or V, F with Y, S with T or A, R with K, G with N or A, K with R, A with S, K or P.

In alternative embodiments, one can also select conservative amino acid substitutions encompassed suitable for amino acids on the interior of a protein or peptide, for example one can use suitable conservative substitutions for amino acids is on the interior of a protein or peptide (i.e. the amino acids are not exposed to a solvent), for example but not limited to, one can use the following conservative substitutions: where Y is substituted with F, T with A or S, I with L or V, W with Y, M with L, N with D, G with A, T with A or S, D with N, I with L or V, F with Y or L, S with A or T and A with S, G, T or V. In some embodiments, non-conservative amino acid substitutions are also encompassed within the term of variants.

In some aspects, the polypeptides are derivatives of the native Cav-1 polypeptide. The term "derivative" as used herein refers to peptides which have been chemically modified, for example but not limited to by techniques such as acetylation, ubiquitination, labeling, pegylation (derivatization with polyethylene glycol), lipidation, glycosylation, amidation, or addition of other molecules. A molecule is also a "derivative" of another molecule when it contains additional chemical moieties not normally a part of the molecule. Such moieties can alter the pH or improve the molecule's solubility, absorption, biological half-life, etc. The moieties can alternatively decrease the toxicity of the molecule, eliminate or attenuate any undesirable side effect of the molecule, etc. Moieties capable of mediating such effects are disclosed in Remington's Pharmaceutical Sciences, 18th edition, A. R. Gennaro, Ed., MackPubl., Easton, PA (1990), incorporated herein, by reference, in its entirety.

The term "functional" when used in conjunction with "derivative" or "variant" refers to a polypeptide of the invention which possesses a biological activity (either functional or structural) that is substantially similar to a biological activity of the entity or molecule it is a functional derivative or functional variant thereof. The term functional derivative is intended to include the fragments, analogues or chemical derivatives of a molecule.

In some aspects, amino acid substitutions can be made in a polypeptide at one or more positions wherein the substitution is for an amino acid having a similar hydrophilicity. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like. Thus such conservative substitution can be made in a polypeptide and will likely only have minor effects on their activity. As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (0.5); histidine −0.5); cysteine (−1.0); methionine (−1.3); valine (−1.5); leucine (−1.8); isoleucine (−1.8); tyrosine (−2.3); phenylalanine (−2.5); tryptophan (−3.4). These values can be used as a guide and thus substitution of amino acids whose hydrophilicity values are within ±2 are preferred, those that are within ±1 are particularly preferred, and those within ±0.5 are even more particularly preferred. Thus, any of the polypeptides described herein may be modified by the substitution of an amino acid, for different, but homologous amino acid with a similar hydrophilicity value. Amino acids with hydrophilicities within +/−1.0, or +/−0.5 points are considered homologous.

The modified Cav-1 peptides may comprise co-translational and post-translational (C-terminal peptide cleavage) modifications, such as, for example, disulfide-bond formation, glycosylation, acetylation, phosphorylation, proteolytic cleavage (e.g., cleavage by furins or metalloproteases), and the like to the extent that such modifications do not affect the anti-inflammatory properties of the isolated peptides or their capacity to improve glycemic control.

In some aspects, the modified Cav-1 peptide comprises non-naturally occurring amino acids. The polypeptides can comprise a combination of naturally occurring and non-naturally occurring amino acids, or may comprise only non-naturally occurring amino acids.

The non-naturally occurring amino acids can include synthetic non-native amino acids, substituted amino acids, or one or more D-amino acids into the peptides (or other components of the composition, with exception for protease recognition sequences) is desirable in certain situations. D-amino acid-containing peptides exhibit increased stability in vitro or in vivo compared to L-amino acid-containing forms. Thus, the construction of peptides incorporating D-amino acids can be particularly useful when greater in vivo or intracellular stability is desired or required. More specifically, D-peptides are resistant to endogenous peptidases and proteases, thereby providing better oral trans-epithelial and transdermal delivery of linked drugs and conjugates, improved bioavailability of membrane-permanent complexes (see below for further discussion), and prolonged intravascular and interstitial lifetimes when such properties are desirable. The use of D-isomer peptides can also enhance transdermal and oral trans-epithelial delivery of linked drugs and other cargo molecules. Additionally, D-peptides cannot be processed efficiently for major histocompatibility complex class II-restricted presentation to T helper cells, and are therefore less likely to induce humoral immune responses in the whole organism. Peptide conjugates can therefore be constructed using, for example, D-isomer forms of cell penetrating peptide sequences, L-isomer forms of cleavage sites, and D-isomer forms of therapeutic peptides.

In addition to the 20 "standard" L-amino acids, D-amino acids or non-standard, modified or unusual amino acids which are well-defined in the art are also contemplated for use in the present disclosure. Phosphorylated amino acids (Ser, Thr, Tyr), glycosylated amino acids (Ser, Thr, Asn), β-amino acids, GABA, ω-amino acids are further contemplated for use in the present disclosure. These include, for example, include β-alanine (β-Ala) and other ω-amino acids such as 3-aminopropionic acid, 2,3-diaminopropionic acid (Dpr), 4-aminobutyric acid and so forth; α-aminoisobutyric acid (Aib); ε-aminohexanoic acid (Aha); δ-aminovaleric acid (Ava); N-methylglycine or sarcosine (MeGly); ornithine (Orn); citrulline (Cit); t-butylalanine (t-BuA); t-butylglycine (t-BuG); N-methylisoleucine (MeIle); phenylglycine (Phg); norleucine (Nle); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); homoarginine (hArg); N-acetyl lysine (AcLys); 2,4-diaminobutyric acid (Dbu); 2,4-diaminobutyric acid (Dab); p-aminophenylalanine (Phe(pNH$_2$)); N-methyl valine (MeVal); homocysteine (hCys), homophenylalanine (hPhe) and homoserine (hSer); hydroxyproline (Hyp), homoproline (hPro), N-methylated amino acids and peptoids (N-substituted glycines).

Carboxy terminal modifications include acylation with carboxylic acids: formic, acetic, propionic, fatty acids (myristic, palmitic, stearic), succinic, benzoic, carbobenzoxy (Cbz); acetylation and biotinylation. Amino terminal modifications include: (i) acylation with carboxylic acids: formic, acetic, propionic, fatty acids (myristic, palmitic, stearic, etc) succinic, benzoic, carbobenzoxy (Cbz); (ii) biotinylation; (iii) amidation; (iv) attachment of dyes such as fluorescein (FITC, FAM, etc.), 7-hydroxy-4-methylcoumarin-3-acetic acid, 7-hydroxycoumarin-3-acetic acid, 7-metoxycoumarin-3-acetic acid and other coumarins; rhodamines (5-carboxyrhodamine 110 or 6G, 5(6)-TAMRA, ROX); N-[4-(4-dimethylamino)phenylazo]benzoic acid (Dabcyl), 2,4-dinitrobenzene (Dnp), 5-dimethylaminonaphthalene-1-sulfonic acid (Dansyl) and other dyes; and (v) polyethyleneglycol.

The polypeptide may be capped at its N and C termini with an acyl (abbreviated "Ac")—and an amido (abbreviated "Am") group, respectively, for example acetyl ($CH_3CO$—) at the N terminus and amido (—$NH_2$) at the C terminus. A broad range of N-terminal capping functions, preferably in a linkage to the terminal amino group, is contemplated, for example: formyl;

alkanoyl, having from 1 to 10 carbon atoms, such as acetyl, propionyl, butyryl;

alkenoyl, having from 1 to 10 carbon atoms, such as hex-3-enoyl;

alkynoyl, having from 1 to 10 carbon atoms, such as hex-5-ynoyl;

aroyl, such as benzoyl or 1-naphthoyl;

heteroaroyl, such as 3-pyrroyl or 4-quinoloyl;

alkylsulfonyl, such as methanesulfonyl;

arylsulfonyl, such as benzenesulfonyl or sulfanilyl;

heteroarylsulfonyl, such as pyridine-4-sulfonyl;

substituted alkanoyl, having from 1 to 10 carbon atoms, such as 4-aminobutyryl;

substituted alkenoyl, having from 1 to 10 carbon atoms, such as 6-hydroxy-hex-3-enoyl;

substituted alkynoyl, having from 1 to 10 carbon atoms, such as 3-hydroxy-hex-5-ynoyl;

substituted aroyl, such as 4-chlorobenzoyl or 8-hydroxynaphth-2-oyl;

substituted heteroaroyl, such as 2,4-dioxo-1,2,3,4-tetrahydro-3-methyl-quinazolin-6-oyl;

substituted alkylsulfonyl, such as 2-aminoethanesulfonyl;

substituted arylsulfonyl, such as 5-dimethylamino-1-naphthalenesulfonyl;

substituted heteroarylsulfonyl, such as 1-methoxy-6-isoquinolinesulfonyl;

carbamoyl or thiocarbamoyl;

substituted carbamoyl (R'—NH—CO) or substituted thiocarbamoyl (R'—NH—CS) wherein R' is alkyl, alkenyl, alkynyl, aryl, heteroaryl, substituted alkyl, substituted alkenyl, substituted alkynyl, substituted aryl, or substituted heteroaryl;

substituted carbamoyl (R'—NH—CO) and substituted thiocarbamoyl (R'—NH—CS) wherein R' is alkanoyl, alkenoyl, alkynoyl, aroyl, heteroaroyl, substituted alkanoyl, substituted alkenoyl, substituted alkynoyl, substituted aroyl, or substituted heteroaroyl, all as above defined.

The C-terminal capping function can either be in an amide or ester bond with the terminal carboxyl. Capping functions that provide for an amide bond are designated as NR$^1$R$^2$ wherein R$^1$ and R$^2$ may be independently drawn from the following group: hydrogen;
  alkyl, preferably having from 1 to 10 carbon atoms, such as methyl, ethyl, isopropyl;
  alkenyl, preferably having from 1 to 10 carbon atoms, such as prop-2-enyl;
  alkynyl, preferably having from 1 to 10 carbon atoms, such as prop-2-ynyl;
  substituted alkyl having from 1 to 10 carbon atoms, such as hydroxyalkyl, alkoxyalkyl, mercaptoalkyl, alkylthioalkyl, halogenoalkyl, cyanoalkyl, aminoalkyl, alkylaminoalkyl, dialkylaminoalkyl, alkanoylalkyl, carboxyalkyl, carbamoylalkyl;
  substituted alkenyl having from 1 to 10 carbon atoms, such as hydroxyalkenyl, alkoxyalkenyl, mercaptoalkenyl, alkylthioalkenyl, halogenoalkenyl, cyanoalkenyl, aminoalkenyl, alkylaminoalkenyl, dialkylaminoalkenyl, alkanoylalkenyl, carboxyalkenyl, carbamoylalkenyl;
  substituted alkynyl having from 1 to 10 carbon atoms, such as hydroxyalkynyl, alkoxyalkynyl, mercaptoalkynyl, alkylthioalkynyl, halogenoalkynyl, cyanoalkynyl, aminoalkynyl, alkylaminoalkynyl, dialkylaminoalkynyl, alkanoylalkynyl, carboxyalkynyl, carbamoylalkynyl;
  aroylalkyl having up to 10 carbon atoms, such as phenacyl or 2-benzoylethyl;
  aryl, such as phenyl or 1-naphthyl;
  heteroaryl, such as 4-quinolyl;
  alkanoyl having from 1 to 10 carbon atoms, such as acetyl or butyryl;
  aroyl, such as benzoyl;
  heteroaroyl, such as 3-quinoloyl;
  OR' or NR'R'' where R' and R'' are independently hydrogen, alkyl, aryl, heteroaryl, acyl, aroyl, sulfonyl, sulfinyl, or SO$_2$—R''' or SO—R''' where R''' is substituted or unsubstituted alkyl, aryl, heteroaryl, alkenyl, or alkynyl.

Capping functions that provide for an ester bond are designated as OR, wherein R may be: alkoxy; aryloxy; heteroaryloxy; aralkyloxy; heteroaralkyloxy; substituted alkoxy; substituted aryloxy; substituted heteroaryloxy; substituted aralkyloxy; or substituted heteroaralkyloxy.

Either the N-terminal or the C-terminal capping function, or both, may be of such structure that the capped molecule functions as a prodrug (a pharmacologically inactive derivative of the parent drug molecule) that undergoes spontaneous or enzymatic transformation within the body in order to release the active drug and that has improved delivery properties over the parent drug molecule (Bundgaard H, Ed: *Design of Prodrugs*, Elsevier, Amsterdam, 1985).

Judicious choice of capping groups allows the addition of other activities on the peptide. For example, the presence of a sulfhydryl group linked to the N- or C-terminal cap will permit conjugation of the derivatized peptide to other molecules.

In yet a further aspect, the peptides or fragments or derivatives thereof can be "retro-inverso peptides." A "retro-inverso peptide" refers to a peptide with a reversal of the direction of the peptide bond on at least one position, i.e., a reversal of the amino- and carboxy-termini with respect to the side chain of the amino acid. Thus, a retro-inverso analogue has reversed termini and reversed direction of peptide bonds while approximately maintaining the topology of the side chains as in the native peptide sequence. The retro-inverso peptide can contain L-amino acids or D-amino acids, or a mixture of L-amino acids and D-amino acids, up to all of the amino acids being the D-isomer. Partial retro-inverso peptide analogues are polypeptides in which only part of the sequence is reversed and replaced with enantiomeric amino acid residues. Since the retro-inverted portion of such an analogue has reversed amino and carboxyl termini, the amino acid residues flanking the retro-inverted portion are replaced by side-chain-analogous a-substituted geminal-diaminomethanes and malonates, respectively. Retro-inverso forms of cell penetrating peptides have been found to work as efficiently in translocating across a membrane as the natural forms. Synthesis of retro-inverso peptide analogues are described in Bonelli, F. et al., *Int J Pept Protein Res.* 24(6):553-6 (1984); Verdini, A and Viscomi, G. C, *J. Chem. Soc. Perkin Trans.* 1:697-701 (1985); and U.S. Pat. No. 6,261,569, which are incorporated herein in their entirety by reference. Processes for the solid-phase synthesis of partial retro-inverso peptide analogues have been described (EP 97994-B) which is also incorporated herein in its entirety by reference.

A polynucleotide or polynucleotide region (or a polypeptide or polypeptide region) has a certain percentage (for example, 80%, 85%, 90%, or 95%) of "sequence identity" or "homology" to another sequence means that, when aligned, that percentage of bases (or amino acids) are the same in comparing the two sequences. This alignment and the percent homology or sequence identity can be determined using software programs known in the art, for example those described in Current Protocols In Molecular Biology (F. M. Ausubel et al., eds., 1987) Supplement 30, section 7.7.18, Table 7.7.1. Preferably, default parameters are used for alignment. A preferred alignment program is BLAST, using default parameters. In particular, preferred programs are BLASTN and BLASTP, using the following default parameters: Genetic code=standard; filter=none; strand=both; cut-off=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR.

A. Multimeric Polypeptides

Embodiments of the present disclosure also include longer polypeptides built from repeating units of a modified Cav-1 variant polypeptide. A polypeptide multimer may comprise different combinations of polypeptide. Such multimeric polypeptides can be made by chemical synthesis or by recombinant DNA techniques as discussed herein. When produced by chemical synthesis, the oligomers preferably have from 2-5 repeats of a core polypeptide sequence, and the total number of amino acids in the multimer should not exceed about 160 residues, preferably not more than 100 residues (or their equivalents, when including linkers or spacers).

B. Peptidomimetics

The modified Cav-1 peptide may be a peptidomimetic compound which mimics the biological effects of the native Cav-1 polypeptide. A peptidomimetic agent may be an unnatural peptide or a non-peptide agent that recreates the stereospatial properties of the binding elements of the native Cav-1 polypeptide such that it has the binding activity and biological activity of the native Cav-1 polypeptide. Similar to a native Cav-1 polypeptide or polypeptide multimer, a peptidomimetic will have a binding face (which interacts with any ligand to which native Cav-1 binds) and a non-binding face.

In some aspects, the present disclosure also includes compounds that retain partial peptide characteristics. For example, any proteolytically unstable bond within a peptide of the invention could be selectively replaced by a non-peptidic element such as an isostere (N-methylation; D-amino acid) or a reduced peptide bond while the rest of the molecule retains its peptidic nature.

Peptidomimetic compounds, either agonists, substrates or inhibitors, have been described for a number of bioactive peptides/polypeptides such as opioid peptides, VIP, thrombin, HIV protease, etc. Methods for designing and preparing peptidomimetic compounds are known in the art (Hruby, V J, *Biopolymers* 33:1073-1082 (1993); Wiley, R A et al., *Med. Res. Rev.* 13:327-384 (1993); Moore et al., *Adv. in Pharmacol* 33:91-141 (1995); Giannis et al., *Adv. in Drug Res.* 29:1-78 (1997). Certain mimetics that mimic secondary structure are described in Johnson et al., In: *Biotechnology and Pharmacy*, Pezzuto et al., Chapman and Hall (Eds.), NY, 1993. These methods are used to make peptidomimetics that possess at least the binding capacity and specificity of the native Cav-1 polypeptide and preferably also possess the biological activity. Knowledge of peptide chemistry and general organic chemistry available to those skilled in the art are sufficient, in view of the present disclosure, for designing and synthesizing such compounds.

For example, such peptidomimetics may be identified by inspection of the three-dimensional structure of a polypeptide of the invention either free or bound in complex with a ligand (e.g., soluble uPAR or a fragment thereof). Alternatively, the structure of a polypeptide of the invention bound to its ligand can be gained by the techniques of nuclear magnetic resonance spectroscopy. Greater knowledge of the stereochemistry of the interaction of the peptide with its ligand or receptor will permit the rational design of such peptidomimetic agents. The structure of a peptide or polypeptide of the invention in the absence of ligand could also provide a scaffold for the design of mimetic molecules.

C. PEGylation

The modified Cav-1 peptides may be conjugated with heterologous polypeptide segments or polymers, such as polyethylene glycol. The polypeptides may be linked to PEG to increase the hydrodynamic radius of the enzyme and hence increase the serum persistence. The polypeptides may be conjugated to any targeting agent, such as a ligand having the ability to specifically and stably bind to an external receptor (U.S. Patent Publ. 2009/0304666).

In certain aspects, methods and compositions of the embodiments related to PEGylation of disclosed polypeptides. PEGylation is the process of covalent attachment of poly(ethylene glycol) polymer chains to another molecule, normally a drug or therapeutic protein. PEGylation is routinely achieved by incubation of a reactive derivative of PEG with the target macromolecule. The covalent attachment of PEG to a drug or therapeutic protein can "mask" the agent from the host's immune system (reduced immunogenicity and antigenicity) or increase the hydrodynamic size (size in solution) of the agent, which prolongs its circulatory time by reducing renal clearance. PEGylation can also provide water solubility to hydrophobic drugs and proteins.

The first step of the PEGylation is the suitable functionalization of the PEG polymer at one or both terminals. PEGs that are activated at each terminus with the same reactive moiety are known as "homobifunctional," whereas if the functional groups present are different, then the PEG derivative is referred as "heterobifunctional" or "heterofunctional." The chemically active or activated derivatives of the PEG polymer are prepared to attach the PEG to the desired molecule.

The choice of the suitable functional group for the PEG derivative is based on the type of available reactive group on the molecule that will be coupled to the PEG. For proteins, typical reactive amino acids include lysine, cysteine, histidine, arginine, aspartic acid, glutamic acid, serine, threonine, and tyrosine. The N-terminal amino group and the C-terminal carboxylic acid can also be used.

The techniques used to form first generation PEG derivatives are generally reacting the PEG polymer with a group that is reactive with hydroxyl groups, typically anhydrides, acid chlorides, chloroformates, and carbonates. In the second generation PEGylation chemistry more efficient functional groups, such as aldehyde, esters, amides, etc., are made available for conjugation.

As applications of PEGylation have become more and more advanced and sophisticated, there has been an increase in need for heterobifunctional PEGs for conjugation. These heterobifunctional PEGs are very useful in linking two entities, where a hydrophilic, flexible, and biocompatible spacer is needed. Preferred end groups for heterobifunctional PEGs are maleimide, vinyl sulfones, pyridyl disulfide, amine, carboxylic acids, and NHS esters.

The most common modification agents, or linkers, are based on methoxy PEG (mPEG) molecules. Their activity depends on adding a protein-modifying group to the alcohol end. In some instances polyethylene glycol (PEG diol) is used as the precursor molecule. The diol is subsequently modified at both ends in order to make a hetero- or homo-dimeric PEG-linked molecule.

Proteins are generally PEGylated at nucleophilic sites, such as unprotonated thiols (cysteinyl residues) or amino groups. Examples of cysteinyl-specific modification reagents include PEG maleimide, PEG iodoacetate, PEG thiols, and PEG vinylsulfone. All four are strongly cysteinyl-specific under mild conditions and neutral to slightly alkaline pH but each has some drawbacks. The thioether formed with the maleimides can be somewhat unstable under alkaline conditions so there may be some limitation to formulation options with this linker. The carbamothioate linkage formed with iodo PEGs is more stable, but free iodine can modify tyrosine residues under some conditions. PEG thiols form disulfide bonds with protein thiols, but this linkage can also be unstable under alkaline conditions. PEG-vinylsulfone reactivity is relatively slow compared to maleimide and iodo PEG; however, the thioether linkage formed is quite stable. Its slower reaction rate also can make the PEG-vinylsulfone reaction easier to control.

Site-specific PEGylation at native cysteinyl residues is seldom carried out, since these residues are usually in the form of disulfide bonds or are required for biological activity. On the other hand, site-directed mutagenesis can be used to incorporate cysteinyl PEGylation sites for thiol-specific linkers. The cysteine mutation must be designed such that it is accessible to the PEGylation reagent and is still biologically active after PEGylation.

Amine-specific modification agents include PEG NHS ester, PEG tresylate, PEG aldehyde, PEG isothiocyanate, and several others. All react under mild conditions and are very specific for amino groups. The PEG NHS ester is probably one of the more reactive agents; however, its high reactivity can make the PEGylation reaction difficult to control on a large scale. PEG aldehyde forms an imine with the amino group, which is then reduced to a secondary amine with sodium cyanoborohydride. Unlike sodium borohydride, sodium cyanoborohydride will not reduce disulfide bonds. However, this chemical is highly toxic and must be handled cautiously, particularly at lower pH where it becomes volatile.

Due to the multiple lysine residues on most proteins, site-specific PEGylation can be a challenge. Fortunately, because these reagents react with unprotonated amino groups, it is possible to direct the PEGylation to lower-pK amino groups by performing the reaction at a lower pH. Generally the pK of the alpha-amino group is 1-2 pH units lower than the epsilon-amino group of lysine residues. By PEGylating the molecule at pH 7 or below, high selectivity for the N-terminus frequently can be attained. However, this is only feasible if the N-terminal portion of the protein is not required for biological activity. Still, the pharmacokinetic benefits from PEGylation frequently outweigh a significant loss of in vitro bioactivity, resulting in a product with much greater in vivo bioactivity regardless of PEGylation chemistry.

There are several parameters to consider when developing a PEGylation procedure. Fortunately, there are usually no more than four or five key parameters. The "design of experiments" approach to optimization of PEGylation conditions can be very useful. For thiol-specific PEGylation reactions, parameters to consider include: protein concentration, PEG-to-protein ratio (on a molar basis), temperature, pH, reaction time, and in some instances, the exclusion of oxygen. (Oxygen can contribute to intermolecular disulfide formation by the protein, which will reduce the yield of the PEGylated product.) The same factors should be considered (with the exception of oxygen) for amine-specific modification except that pH may be even more critical, particularly when targeting the N-terminal amino group.

For both amine- and thiol-specific modifications, the reaction conditions may affect the stability of the protein. This may limit the temperature, protein concentration, and pH. In addition, the reactivity of the PEG linker should be known before starting the PEGylation reaction. For example, if the PEGylation agent is only 70 percent active, the amount of PEG used should ensure that only active PEG molecules are counted in the protein-to-PEG reaction stoichiometry.

D. Fusion Proteins

Certain embodiments of the present invention concern fusion proteins of the modified Cav-1 peptides. These molecules may have the polypeptides of the embodiments linked at the N- or C-terminus to a heterologous domain. For example, fusions may also employ leader sequences from other species to permit the recombinant expression of a protein in a heterologous host. Fusion proteins can comprise a half-life extender. Another useful fusion includes the addition of a protein affinity tag, such as a serum albumin affinity tag or six histidine residues, or an immunologically active domain, such as an antibody epitope, preferably cleavable, to facilitate purification of the fusion protein. Non-limiting affinity tags include polyhistidine, chitin binding protein (CBP), maltose binding protein (MBP), and glutathione-S-transferase (GST).

In a particular embodiment, the peptide of the embodiments may be linked to a peptide that increases the in vivo half-life, such as an XTEN® polypeptide (Schellenberger et al., 2009), IgG Fc domain, albumin, or albumin binding peptide.

Methods of generating fusion proteins are well known to those of skill in the art. Such proteins can be produced, for example, by de novo synthesis of the complete fusion protein, or by attachment of the DNA sequence encoding the heterologous domain, followed by expression of the intact fusion protein.

Production of fusion proteins that recover the functional activities of the parent proteins may be facilitated by connecting genes with a bridging DNA segment encoding a peptide linker that is spliced between the polypeptides connected in tandem. The linker would be of sufficient length to allow proper folding of the resulting fusion protein.

1. Linkers

In certain embodiments, the polypeptide of the embodiments may be chemically conjugated using bifunctional cross-linking reagents or fused at the protein level with peptide linkers.

Bifunctional cross-linking reagents have been extensively used for a variety of purposes, including preparation of affinity matrices, modification and stabilization of diverse structures, identification of ligand and receptor binding sites, and structural studies. Suitable peptide linkers may also be used to link the polypeptide of the embodiments, such as Gly-Ser linkers.

Homobifunctional reagents that carry two identical functional groups proved to be highly efficient in inducing cross-linking between identical and different macromolecules or subunits of a macromolecule, and linking of polypeptide ligands to their specific binding sites. Heterobifunctional reagents contain two different functional groups. By taking advantage of the differential reactivities of the two different functional groups, cross-linking can be controlled both selectively and sequentially. The bifunctional cross-linking reagents can be divided according to the specificity of their functional groups, e.g., amino-, sulfhydryl-, guanidine-, indole-, carboxyl-specific groups. Of these, reagents directed to free amino groups have become especially popular because of their commercial availability, ease of synthesis, and the mild reaction conditions under which they can be applied.

A majority of heterobifunctional cross-linking reagents contain a primary amine-reactive group and a thiol-reactive group. In another example, heterobifunctional cross-linking reagents and methods of using the cross-linking reagents are described (U.S. Pat. No. 5,889,155, specifically incorporated herein by reference in its entirety). The cross-linking reagents combine a nucleophilic hydrazide residue with an electrophilic maleimide residue, allowing coupling, in one example, of aldehydes to free thiols. The cross-linking reagent can be modified to cross-link various functional groups.

Additionally, any other linking/coupling agents and/or mechanisms known to those of skill in the art may be used to combine polypeptides of the embodiments, such as, for example, antibody-antigen interaction, avidin biotin linkages, amide linkages, ester linkages, thioester linkages, ether linkages, thioether linkages, phosphoester linkages, phosphoramide linkages, anhydride linkages, disulfide linkages, ionic and hydrophobic interactions, bispecific antibodies and antibody fragments, or combinations thereof.

It is preferred that a cross-linker having reasonable stability in blood will be employed. Numerous types of disulfide-bond containing linkers are known that can be successfully employed to conjugate targeting and therapeutic/preventative agents. Linkers that contain a disulfide bond that is sterically hindered may prove to give greater stability in vivo. These linkers are thus one group of linking agents.

In addition to hindered cross-linkers, non-hindered linkers also can be employed in accordance herewith. Other useful cross-linkers, not considered to contain or generate a protected disulfide, include SATA, SPDP, and 2-iminothiolane (Wawrzynczak and Thorpe, 1987). The use of such cross-linkers is well understood in the art. Another embodiment involves the use of flexible linkers.

Once chemically conjugated, the peptide generally will be purified to separate the conjugate from unconjugated agents and from other contaminants. A large number of purification techniques are available for use in providing conjugates of a sufficient degree of purity to render them clinically useful.

Purification methods based upon size separation, such as gel filtration, gel permeation, or high performance liquid chromatography, will generally be of most use. Other chromatographic techniques, such as Blue-Sepharose separation, may also be used.

Conventional methods to purify the fusion proteins from inclusion bodies may be useful, such as using weak detergents, such as sodium N-lauroyl-sarcosine (SLS).

2. Cell Penetrating and Membrane Translocation Peptides

Furthermore, in certain aspects, the modified Cav-1 peptides may further comprise a cell-binding domain or cell penetrating peptide (CPP). As used herein the terms "cell penetrating peptide" and "membrane translocation domain" are used interchangeably and refer to segments of polypeptide sequence that allow a polypeptide to cross the cell membrane (e.g., the plasma membrane in the case a eukaryotic cell). Examples of CPP segments include, but are not limited to, segments derived from HIV Tat (e.g., GRKKRRQRRRPPQ (SEQ ID NO: 21)), herpes virus VP22, the *Drosophila* Antennapedia homeobox gene product, protegrin I, Penetratin (RQIKIWFQNRRMKWKK (SEQ ID NO: 22)) or melittin (GIGAVLKVLTTGLPAL-ISWIKRKRQQ (SEQ ID NO: 23)). In certain aspects the CPP comprises the T1 (TKIESLKEHG (SEQ ID NO: 24)), T2 (TQIENLKEKG (SEQ ID NO: 25)), (AALEALAEAL-EALAEALEALAEAAAA (SEQ ID NO: 26)) or INF7 (GLFEAIEGFIENGWEGMIEGWYGCG (SEQ ID NO: 27)) CPP sequence.

III. METHODS OF USE

One aspect of the present invention relates to the use of polypeptides described herein and mutants, variants, analogs or derivatives thereof. Specifically, these methods relate to administering any one of the polypeptides as described herein or their pharmaceutically acceptable modifications in a pharmaceutically acceptable carrier to a subject, a composition for use in the treatment of treating or preventing a disease, injury or infection of the lungs (e.g., a fibrotic condition of the lungs), said composition comprising a polypeptide of the embodiments in pharmaceutically acceptable carrier.

A. Pharmaceutical Compositions

It is contemplated that the modified Cav-1 peptides can be administered systemically or locally to inhibit cell apoptosis and for the treatment and prevention damage to lung tissues. They can be administered intravenously, intrathecally, and/or intraperitoneally. In particular aspects, the polypeptides are delivered locally to the airway, such as administration of a nebulized formulation or a dry powder formulation for inhalation. They can be administered alone or in combination with anti-fibrotic compounds.

The modified Cav-1 peptide may be administered in combination, simultaneously or sequentially with at least one additional therapeutic for lung fibrosis. The additional therapeutic may be an NSAID, steroid, DMARD, immunosuppressive, biologic response modulators, bronchodilator or antifibrotic agent such as pirfenedone, an agent whose antifibrotic mechanism of action is not fully understood but may involve blockade of TGF-beta, nintedanib, a broad tyrosine kinase blocker or any other antifibrotic agent. Suitable NSAIDS are selected from the non-selective COX-inhibitors acetylsalicyclic acid, mesalazin, ibuprofen, naproxen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen, indomethacin, sulindac, tolmetin, zomepirac, nabumetone, diclofenac, fenclofenac, alclofenac, bromfenac, ibufenac, aceclofenac, acemetacin, fentiazac, clidanac, etodolac, oxpinac, mefenamic acid, meclofenamic acid, flufenamic acid, nifluminic acid, tolfenamic acid, diflunisal, flufenisal, piroxicam, tenoxicam, lornoxicam and nimesulide and the pharmaceutically acceptable salts thereof, the selective COX 2-inhibitors meloxicam, celecoxib and rofecoxib and the pharmaceutically acceptable salts thereof. Suitable steroids are prednisone, prednisolone, methylprednisolone, dexamethasone, budenoside, fluocortolone and triamcinolone. Suitable DMARDs are sulfasalazine, olsalazine, chloroquin, gold derivatives (Auranofin), D-penicillamine and cytostatics such as methotrexate and cyclophosphamide. Suitable immunsuppressives are cyclosporine A and derivatives thereof, mycophenolatemofetil, FK 506, OKT-3, ATG, 15-desoxyspergualin, mizoribine, misoprostol, rapamycin, reflunomide and azathioprine. Suitable biologic response modifiers are interferon 13, anti-TNF-α (Etanercept), IL-10, anti-CD3 or anti-CD25. Suitable bronchodilators are ipratropiumbromide, oxytropiumbromide, tiotropiumbromide, epinephrinehydrochloride, salbutamole, terbutalinsulfate, fenoterolhydrobromide, salmeterole and formoterole. In such combinations each active ingredient can be administered either in accordance with its usual dosage range or a dose below its usual dosage range. The dosage for the combined NSAIDs, steroids, DMARDs, immunosuppressives and biologic response modifiers is appropriately 1/50 of the lowest dose normally recommended up to 1/1 of the normally recommended dosage, preferably 1/20 to 1/2 and more preferably 1/10 to 1/5. The normally recommended dose for the combined drug should be understood to be the dose disclosed for example in Rote Liste® 2002, Editio Cantor Verlag Aulendorf, Germany, or in Physician's Desk Reference.

Where clinical applications are contemplated, it may be necessary to prepare pharmaceutical compositions comprising proteins, antibodies, and drugs in a form appropriate for the intended application. Generally, pharmaceutical compositions may comprise an effective amount of one or more of the polypeptides of the embodiments or additional agents dissolved or dispersed in a pharmaceutically acceptable carrier. The phrases "pharmaceutical or pharmacologically acceptable" refers to molecular entities and compositions that do not produce an adverse, allergic, or other untoward reaction when administered to an animal, such as, for example, a human, as appropriate. The preparation of a pharmaceutical composition that contains at least one polypeptide of the embodiments isolated by the method disclosed herein, or additional active ingredient will be known to those of skill in the art in light of the present disclosure, as exemplified by Remington's Pharmaceutical Sciences, 18th Ed., 1990, incorporated herein by reference. Moreover, for animal (e.g., human) administration, it will be understood that preparations should meet sterility, pyrogenicity, general safety, and purity standards as required by the FDA Office of Biological Standards.

As used herein, "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, gels, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed., 1990, incorporated herein by reference). Except insofar as any conventional carrier is incompatible with the active ingredient, its use in the pharmaceutical compositions is contemplated.

Certain embodiments of the present invention may comprise different types of carriers depending on whether it is to be administered in solid, liquid, or aerosol form, and whether it needs to be sterile for the route of administration, such as injection. The compositions can be administered intravenously, intrathecally, intradermally, transdermally, intrathecally, intraarterially, intraperitoneally, intranasally, intravaginally, intrarectally, intramuscularly, subcutaneously, mucosally, orally, topically, locally, by inhalation (e.g., inhalation of a nebulized or dry powder formulation), by injection, by infusion, by continuous infusion, by localized perfusion bathing target cells directly, via a catheter, via a lavage, in lipid compositions (e.g., liposomes), or by other methods or any combination of the forgoing as would be known to one of ordinary skill in the art (see, for example, Remington's Pharmaceutical Sciences, 18th Ed., 1990, incorporated herein by reference).

The modified polypeptides may be formulated into a composition in a free base, neutral, or salt form. Pharmaceutically acceptable salts include the acid addition salts, e.g., those formed with the free amino groups of a proteinaceous composition, or which are formed with inorganic acids, such as, for example, hydrochloric or phosphoric acids, or such organic acids as acetic, oxalic, tartaric, or mandelic acid. Salts formed with the free carboxyl groups can also be derived from inorganic bases, such as, for example, sodium, potassium, ammonium, calcium, or ferric hydroxides; or such organic bases as isopropylamine, trimethylamine, histidine, or procaine. Upon formulation, solutions will be administered in a manner compatible with the dosage formulation and in such amount as is therapeutically effective. The formulations are easily administered in a variety of dosage forms, such as formulated for parenteral administrations, such as injectable solutions, or aerosols for delivery to the lungs, or formulated for alimentary administrations, such as drug release capsules and the like.

Further in accordance with certain aspects of the present invention, the composition suitable for administration may be provided in a pharmaceutically acceptable carrier with or without an inert diluent. The carrier should be assimilable and includes liquid, semi-solid, i.e., pastes, or solid carriers. Except insofar as any conventional media, agent, diluent, or carrier is detrimental to the recipient or to the therapeutic effectiveness of a composition contained therein, its use in administrable composition for use in practicing the methods is appropriate. Examples of carriers or diluents include fats, oils, water, saline solutions, lipids, liposomes, resins, binders, fillers, and the like, or combinations thereof. The composition may also comprise various antioxidants to retard oxidation of one or more component. Additionally, the prevention of the action of microorganisms can be brought about by preservatives, such as various antibacterial and antifungal agents, including but not limited to parabens (e.g., methylparabens, propylparabens), chlorobutanol, phenol, sorbic acid, thimerosal or combinations thereof.

In accordance with certain aspects of the present invention, the composition is combined with the carrier in any convenient and practical manner, i.e., by solution, suspension, emulsification, admixture, encapsulation, absorption, and the like. Such procedures are routine for those skilled in the art.

In a specific embodiment of the present invention, the composition is combined or mixed thoroughly with a semi-solid or solid carrier. The mixing can be carried out in any convenient manner, such as grinding. Stabilizing agents can be also added in the mixing process in order to protect the composition from loss of therapeutic activity, i.e., denaturation in the stomach. Examples of stabilizers for use in a composition include buffers, amino acids, such as glycine and lysine, carbohydrates or lyoprotectants, such as dextrose, mannose, galactose, fructose, lactose, sucrose, maltose, sorbitol, mannitol, etc.

In some aspects, a pharmaceutical formulation comprises one or more surfactant. Surfactants used in accordance with the disclosed methods include ionic and non-ionic surfactants. Representative non-ionic surfactants include polysorbates such as TWEEN®-20 and TWEEN-80® surfactants (ICI Americas Inc. of Bridgewater, N.J.); poloxamers (e.g., poloxamer 188); TRITON® surfactants (Sigma of St. Louis, Mo.); sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palnidopropyl-, or (e.g., lauroamidopropyl); myristamidopropyl-, palmidopropyl-, or isostearamidopropyl-dimethylamine; sodium methyl cocoyl-, or disodium methyl oleyl-taurate; MONAQUAT™ surfactants (Mona Industries Inc. of Paterson, N.J.); polyethyl glycol; polypropyl glycol; block copolymers of ethylene and propylene glycol such as PLURONIC® surfactants (BASF of Mt. Olive, N.J.); oligo (ethylene oxide) alkyl ethers; alkyl (thio) glucosides, alkyl maltosides; and phospholipids. For example, the surfactant can be present in a formulation in an amount from about 0.01% to about 0.5% (weight of surfactant relative to total weight of other solid components of the formulation; "w/w"), from about 0.03% to about 0.5% (w/w), from about 0.05% to about 0.5% (w/w), or from about 0.1% to about 0.5% (w/w). However, in further aspects, a pharmaceutical formulation of the embodiments is essentially free of non-ionic surfactants or essentially free of all surfactants.

With respect to the therapeutic methods of the invention, it is not intended that the administration of the one or more peptides as disclosed herein or a mutant, variant, analog or derivative thereof and be limited to a particular mode of administration, dosage, or frequency of dosing; the present invention contemplates all modes of administration, including intramuscular, intravenous, intraperitoneal, intravesicular, intraarticular, intralesional, subcutaneous, or any other route sufficient to provide a dose adequate to treat the inflammation-related disorder. The therapeutic may be administered to the patient in a single dose or in multiple doses. When multiple doses are administered, the doses may be separated from one another by, for example, one hour, three hours, six hours, eight hours, one day, two days, one week, two weeks, or one month. For example, the therapeutic may be administered for, e.g., 2, 3, 4, 5, 6, 7, 8, 10, 15, 20, or more weeks. It is to be understood that, for any particular subject, specific dosage regimes should be adjusted over time according to the individual need and the professional judgment of the person administering or supervising the administration of the compositions. For example, the dosage of the therapeutic can be increased if the lower dose does not provide sufficient therapeutic activity.

While the attending physician ultimately will decide the appropriate amount and dosage regimen, therapeutically effective amounts of the one or more polypeptides as disclosed herein or a mutant, variant, analog or derivative thereof may be provided at a dose of 0.0001, 0.01, 0.01 0.1, 1, 5, 10, 25, 50, 100, 500, or 1,000 mg/kg or g/kg. Effective doses may be extrapolated from dose-response curves derived from in vitro or animal model test bioassays or systems.

Dosages for a particular patient or subject can be determined by one of ordinary skill in the art using conventional considerations, (e.g., by means of an appropriate, conventional pharmacological protocol). A physician may, for example, prescribe a relatively low dose at first, subsequently increasing the dose until an appropriate response is obtained. The dose administered to a patient is sufficient to effect a beneficial therapeutic response in the patient over time, or, e.g., to reduce symptoms, or other appropriate activity, depending on the application. The dose is determined by the efficacy of the particular formulation, and the activity, stability or serum half-life of the one or more polypeptides as disclosed herein or a mutant, variant, analog or derivative thereof and the condition of the patient, as well as the body weight or surface area of the patient to be treated.

In some aspects, a subject is given a single dose, given once daily for treating a subject, preferably a mammal, more preferably human who his suffering from or susceptible to pulmonary fibrosis resulting therefrom is between about 0.2 mg/kg and about 250 mg/kg, such as between about 10 mg/kg and about 50 mg/kg, for example, via instillation (by inhalation). Such a dose can be administered daily for anywhere from about 3 days to one or more weeks. Chronic administration is also possible, though the dose may need to be adjusted downward as is well-understood in the art. The foregoing ranges are, however, suggestive, as the number of variables in an individual treatment regime is large, and considerable excursions from these preferred values are expected.

For continuous administration, e.g., by a pump system such as an osmotic pump that was used in some of the experiments described below, a total dosage for a time course of about 1-2 weeks is preferably in the range of 1 mg/kg to 1 g/kg, preferably 20-300 mg/kg, more preferably 50-200 mg/kg. After such a continuous dosing regimen, the total concentration of the active compound is preferably in the range of about 0.5 to about 50 µM, preferably about 1 to about 10 µM.

An effective concentration of the active compound for inhibiting or preventing inhibiting apoptosis in vitro is in the range of about 0.5 nM to about 100 nM, more preferably from about 2 nM to about 20 nM. Effective doses and optimal dose ranges may be determined in vitro using the methods described herein.

B. Aerosol Dispersion and Nebulizing Devices

The formulations can be aerosolized using any suitable device, including but not limited to a jet nebulizer, an ultrasonic nebulizer, a metered dose inhaler (MDI), and a device for aerosolization of liquids by forced passage through a jet or nozzle (e.g., AERX® drug delivery devices by Aradigm of Hayward, Calif.). Furthermore, the compounds can be formulated as dry powders for delivery using a dry powder inhaler device. For delivery of a formulation to a subject, as described further herein below, an pulmonary delivery device can also include a ventilator, optionally in combination with a mask, mouthpiece, mist inhalation apparatus, and/or a platform that guides users to inhale correctly and automatically deliver the drug at the right time in the breath. Representative aerosolization devices that can be used in accordance with the methods of the present invention include but are not limited to those described in U.S. Pat. Nos. 6,357,671; 6,354,516; 6,241,159; 6,044,841; 6,041,776; 6,016,974; 5,823,179; 5,797,389; 5,660,166; 5,355,872; 5,284,133; and 5,277,175 and U.S. Published Patent Application Nos. 20020020412 and 20020020409.

Using a jet nebulizer, compressed gas from a compressor or hospital air line is passed through a narrow constriction known as a jet. This creates an area of low pressure, and liquid medication from a reservoir is drawn up through a feed tube and fragmented into droplets by the air stream. Only the smallest drops leave the nebulizer directly, while the majority impact on baffles and walls and are returned to the reservoir. Consequently, the time required to perform jet nebulization varies according to the volume of the composition to be nebulized, among other factors, and such time can readily be adjusted by one of skill in the art.

A metered dose inhalator (MDI) can be used to deliver a composition of the invention in a more concentrated form than typically delivered using a nebulizer. For optimal effect, MDI delivery systems require proper administration technique, which includes coordinated actuation of aerosol delivery with inhalation, a slow inhalation of about 0.5-0.75 liters per second, a deep breath approaching inspiratory capacity inhalation, and at least 4 seconds of breath holding. Pulmonary delivery using a MDI is convenient and suitable when the treatment benefits from a relatively short treatment time and low cost. Optionally, a formulation can be heated to about 25° C. to about 90° C. during nebulization to promote effective droplet formation and subsequent delivery. See e.g., U.S. Pat. No. 5,299,566.

Aerosol compositions of the embodiments comprise droplets of the composition that are a suitable size for efficient delivery within the lung. In some cases, a surfactant formulation is delivered to lung bronchi, more preferably to bronchioles, still more preferably to alveolar ducts, and still more preferably to alveoli. Aerosol droplets are typically less than about 15 µm in diameter, less than about 10 µm in diameter, less than about 5 µm in diameter, or less than about 2 µm in diameter. For efficient delivery to alveolar bronchi of a human subject, an aerosol composition may preferably comprise droplets having a diameter of about 1 µm to about 5 µm.

Droplet size can be assessed using techniques known in the art, for example cascade, impaction, laser diffraction, and optical patternation. See McLean et al. (2000) *Anal Chem* 72:4796-804, Fults et al. (1991) *J Pharm Pharmacol* 43:726-8, and Vecellio None et al. (2001) *J Aerosol Med* 14:107-14.

Protein stability following aerosolization can be assessed using known techniques in the art, including size exclusion chromatography; electrophoretic techniques; spectroscopic techniques such as UV spectroscopy and circular dichroism spectroscopy, and protein activity (measured in vitro or in vivo). To perform in vitro assays of protein stability, an aerosol composition can be collected and then distilled or absorbed onto a filter. To perform in vivo assays, or for pulmonary administration of a composition to a subject, a device for aerosolization is adapted for inhalation by the subject. For example, protein stability can be assessed by determining the level of protein aggregation. Preferably, an aerosol composition of the invention is substantially free of protein aggregates. The presence of soluble aggregates can be determined qualitatively using DLS (DynaPro-801TC, ProteinSolutions Inc. of Charlottesville, Va.) and/or by UV spectrophotometry.

The term "vibrating mesh nebulizer" refers herein to any nebulizer that operates on the general principle of using a vibrating mesh or plate with multiple aperatures (an aperture plate) to generate a fine-particle, low-velocity aerosol. Some nebulizers may contain a mesh/membrane with between 1000 and 7000 holes, which mesh/membrane vibrates at the top of a liquid reservoir (see, e.g., U.S. Patent Publn. 20090134235 and Waldrep and Dhand 2008, each incorporated herein by reference). In some embodiments, the vibrating mesh nebulizer is an AERONEB® Professional Nebulizer, Omron MICROAIR®, Pari EFLOW® or an EZ Breathe Atomizer. In some aspects, a vibrating mesh nebulizer has a vibrating frequency of between about 50-250 kHz, 75-200 kHz 100-150 kHz or about 120 kHz. These devices have a high efficiency of delivering aerosol to the lung and the volume of liquid remaining in these devices is minimal, which is an advantage for expensive and potent compounds like plasminogen activators.

In certain aspects, a nebulized composition of the embodiments is produced using a vibrating mesh nebulizer. For example, the composition can be produced with an active vibrating mesh nebulizer (e.g., an Aeroneb® Professional Nebulizer System). Descriptions of such system and there operation can be found, for instance, in U.S. Pat. Nos. 6,921,020; 6,926,208; 6,968,840; 6,978,941; 7,040,549; 7,083,112; 7,104,463; and 7,360,536, each of which is incorporated herein by reference in its entirety. In yet further aspects, a composition of the embodiments can be produced with a passive vibrating mesh nebulizer, such as the Omron MicroAir® or the EZ Breathe Atomizer.

IV. PULMONARY CONDITIONS FOR TREATMENT

Modified peptides of the present invention can be used to treat a variety of pulmonary conditions. Pulmonary conditions for treatment may be acute or chronic. Acute pulmonary conditions may be acute lung injury, infection or chemical-induced. Chronic pulmonary conditions maybe the result of injury, infection or disease.

A. Lung Injuries

In some aspects, the subject has an acute lung injury (ALI) or infection or a chemical-induced lung injury. In specific aspects, the subject has acute respiratory distress syndrome (ARDS), inhalational smoke induced acute lung injury (ISALI), bronchiectasis, inhalational toxin-induced airway disease (e.g., chlorine or other induced airways disease), exposure to mustard gas, exposure to particulate matter (e.g., silica dust), bronchiolitis obliterans, bronchiolitis obliterans organizing pneumonia, drug induced lung disease and accelerated pulmonary fibrosis (e.g., that occurs after acute lung injury including ARDS). Acute lung injury (ALI) is a serious medical problem amongst American military personnel. ALI during combat can result from very broad etiologies.

ALI from inhalational injury has been treated with inhaled anticoagulants, steroids, beta-agonists, high frequency ventilation, and extra-corporeal membrane oxygenation, with variable and, in general, suboptimal results. No effective preventive measures are available other than barriers with respiratory masks. The management of ARDS has progressed significantly but remains largely supportive with watchful waiting for endogenous healing mechanisms to take effect; and in-hospital mortality remains above 40% (Matthay et al., 2012). Survivors of ALI often suffer chronic respiratory disability with reduced quality of life. Any modalities that can accelerate recovery and/or prevent later complications such as chronic respiratory insufficiency and pulmonary fibrosis will be highly desirable. There is a dire need to improve the early diagnosis and much more importantly, prevention and therapy of ALI. The pathophysiology of ALI from direct inhalational lung injury or ARDS consequent to systemic illness is extremely complex and heterogeneous, encompassing systemic as well as local cardiopulmonary factors such as increased membrane permeability, influx of inflammatory cytokines, oxidative cellular damage, compartmental fluid shifts, deranged ion channels, and many others (Matthay et al., 2012). Clearly, novel treatments are needed for treating and preventing lung disorders such as ALI.

In some embodiments, there is provided a method of treating or preventing acute lung injury, lung infection or lung disease in a subject comprising administering to the subject an effective amount of a variant polypeptide comprising at least one amino acid substitution, deletion of insertion relative to the amino acid sequence of FTTFTVT (SEQ ID NO:2), wherein the variant polypeptide maintains the biological activity of caveolin-1 (Cav-1). In some aspects, a method of administering a pharmaceutical formulation of the embodiments comprises nebulizing a solution comprising a variant polypeptide. In particular aspects, the subject is a human.

B. Lung Diseases

Lung diseases include cystic fibrosis, chronic obstructive pulmonary disease (COPD), asthma, bronchiolitis obliterans, plastic bronchitis, and pulmonary infections, collagen vascular lung disease (e.g., from lupus, scleroderma or mixed connective tissue disease), interstitial lung disease (e.g., idiopathic pulmonary fibrosis or sarcoidosis), as well as acute and chronic lung injury leading to fibrosis (Murray et al., 1997; Rabe et al., 2007; Tsushima et al., 2009). These diseases constitute the third leading cause of death worldwide.

Cystic fibrosis is an inherited disease of the exocrine glands and exocrine sweat glands which primarily affects the digestive and respiratory systems. This disease usually characterized by chronic respiratory infections, pancreatic insufficiency, abnormally viscid mucous secretions and premature death. Cystic fibrosis (CF) is characterized by progressive airflow obstruction. Subsets of individuals with CF also develop airway hyper-responsiveness to inhaled cholinergic agonists (Weinberger, 2002 and Mitchell et al., 1978) and reversibility of airflow limitation in response to bronchodilators (van Haren et al., 1991 and van Haren et al., 1992). The presence of bronchial hyper-responsiveness and airway obstruction suggest a possible shared etiology of disease between CF and other diseases of airway narrowing such as asthma or chronic obstructive pulmonary disease (COPD) where airway smooth muscle dysfunction is thought to contribute to the disease processes.

A pulmonary infection may be a bacterial infection. The infectious bacteria may be Pseudomonas aeruginosa, *Bacillus anthraces, Listeria monocytogenes, Staphylococcus aureus, Salmenellosis, Yersina pestis, Mycobacterium leprae, M. africanum, M. asiaticum, M. aviuin-intracellulaire, M. chelonei abscessus, M. fallax, M. fortuitum, M. kansasii, M. leprae, M. malmoense, M. shimoidei, M. simiae, M. szulgai, M. xenopi, M. tuberculosis, Brucella melitensis,*

*Brucella suis, Brucella abortus, Brucella canis, Legionella pneumonophilia, Francisella tularensis, Pneurnocystis carinii, mycoplasma,* or *Burkholderia cepacia.* The bacterial infection may result in pneumonia.

Chronic obstructive pulmonary disease (COPD) is a term used to classify two major airflow obstruction disorders: chronic bronchitis and emphysema. Approximately 16 million Americans have COPD, 80-90% of them were smokers throughout much of their lives. COPD is a leading cause of death in the U.S., accounting for 122,283 deaths in 2003. The cost to the USA for COPD was approximately $20.9 billion in direct health care expenditures in 2003. Chronic bronchitis is inflammation of the bronchial airways. The bronchial airways connect the trachea with the lungs. When inflamed, the bronchial tubes secrete mucus, causing a chronic cough.

In emphysema, the alveolar sacs are overinflated as a result of damage to the elastin skeleton of the lung. Inflammatory cells in emphysematous lung release elastase enzymes, which degrade or damage elastin fibers within the lung matrix. Emphysema has a number of causes, including smoking, exposure to environmental pollutants, alpha-one antitrypsin deficiency, and aging.

Bronchiolitis is most commonly caused by viral lower respiratory tract infections, and primarily characterized by acute inflammation, edema, necrosis of epithelial cells lining small airways, and increased mucus production (Ralston et al., 2014). Signs and symptoms typically begin with rhinitis and cough, which may progress to tachypnea, wheezing, rales, use of accessory muscles, and/or nasal flaring.

Bronchiolitis obliterans is a progressive airflow reduction as a result of abnormal remodeling of the small airways in the lungs (Meyer et al., 2014). Bronchiolitis obliterans syndrome is a major complication of lung transplantations, and is often used to describe a delayed allograft dysfunction that results in persistent decline in forced expiratory volume and force that is not caused by other known causes (Meyer et al., 2014).

The term "asthma" may refer to acute asthma, chronic asthma, intermittent asthma, mild persistent asthma, moderate persistent asthma, severe persistent asthma, chronic persistent asthma, mild to moderate asthma, mild to moderate persistent asthma, mild to moderate chronic persistent asthma, allergic (extrinsic) asthma, non-allergic (intrinsic) asthma, nocturnal asthma, bronchial asthma, exercise induced asthma, occupational asthma, seasonal asthma, silent asthma, gastroesophageal asthma, idiopathic asthma and cough variant asthma. During asthma, the airways are persistently inflamed and may occasionally spasm.

V. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Cav-1 Peptide Solubility

In order to determine which peptides may be most soluble in a liquid formulation, 50 mg of each Cav-1 peptide was dissolved in 5 mL of Tris Buffered Saline, pH 7.51. Each sample was vortexed to help the sample dissolve completely. The absorbance at 600 nm was measured immediately after dissolution of the peptides for insoluble peptides, or after 10 minutes for soluble peptides. Absorbance was measured again after 10 minutes for insoluble peptides except for samples APi2348, APi2352, APi2353 which were measured a second time at 15 minutes, 5 minutes, or 15 minutes after dissolution, respectively. Sample APi2345 was measured only after 20 minutes following dissolution, as the dissolution was incomplete (Table 2). pH was also tested after 24 hours.

Samples APi2350, APi2354, APi2355, and APi2356 had increased solubility at pH 7.51 compared to other tested peptides (Table 2). pH remained stable at roughly pH 7.5 for all samples after 24 hours.

TABLE 2

Absorbance of peptides dissolved in TBS, pH 7.51.

| Sample name | Peptide sequence | Dissolve (Y/N) | UV (Abs) at dissolution | UV (Abs) after rest |
|---|---|---|---|---|
| APi2344 | FTTFTVT-NH2 (SEQ ID NO: 11) | N | 2.409 | 1.437 |
| APi2345 | FTTFTVTK-NH2 (SEQ ID NO: 12) | N | | 1.058 |
| APi2346 | KASFTTFTVTK-NH2 (SEQ ID NO: 13) | N | 1.648 | 1.622 |
| APi2347 | Ac-KASFTTFTVTK-NH2 (SEQ ID NO: 14) | N | 2.347 | 2.284 |
| APi2348 | OASFTTFTVTK-NH2 (SEQ ID NO: 15) | N | 0.846 | 0.530 |
| APi2349 | Ac-OASFTTFTVTK-NH2 (SEQ ID NO: 20) | N | 1.870 | 1.827 |
| APi2350 | KASFTTFTVTKGS-NH2 (SEQ ID NO: 4) | Y | | 0.004 |
| APi2351 | Ac-KASFTTFTVTKGS-NH2 (SEQ ID NO: 17) | N | 2.523 | 2.377 |
| APi2352 | DSGKASFTTFTVTK-NH2 (SEQ ID NO: 18) | N | 2.468 | 2.398 |
| APi2353 | Ac-DSGKASFTTFTVTK-NH2 (SEQ ID NO: 19) | N | 3.000 | 3.000 |

TABLE 2-continued

Absorbance of peptides dissolved in TBS, pH 7.51.

| Sample name | Peptide sequence | Dissolve (Y/N) | UV (Abs) at dissolution | UV (Abs) after rest |
|---|---|---|---|---|
| APi2354 | aaEGKASFTTFTVTKGSaa-NH2 (SEQ ID NO: 7) | Y | 0.008 | 0.007 |
| APi2355 | Ac-aaEGKASFTTFTVTKGSaa-NH2 (SEQ ID NO: 8) | Y | 0.000 | 0.000 |
| APi2356 | OASFTTFTVTOS-NH2 (SEQ ID NO: 9) | Y | 0.001 | -0.002 |
| APi2357 | Ac-OASFTTFTVTOS-NH2 (SEQ ID NO: 10) | N | 2.293 | 2.149 |

*a = D-Alanine; O = Ornithine

Example 2—Cav-1 Peptides Increase Smooth Muscle Actin Production

Cav-1 peptides were dissolved in DMSO to make 10 mM stock solutions. 10 mM stock solutions of each peptide were then diluted in HBSS to make 900 µM working stock solutions. The DMSO resuspended polypeptides as well as the working stocks were stored at −20 deg C. For culture media, working stocks were added to DMEM culture media to a final concentration of 10 µM of the Cav-1 peptide.

Idiopathic Pulmonary Fibrosis (IPF) cell line 2051 was purchased and IPF cells from the fourth passage were seeded in 100 mm plates containing DMEM, 10% FBS, and 1% P/S. IPF cells were washed with 4 mL DMEM+1% P/S and serum starved overnight. Cells were then treated for 2 days with either 44 uL HBSS (negative control), 10 uM LTI-03 (SEQ ID NO: 2), 90 uM LTI-03 (positive control), 10 uM APi2350, 10 uM APi2354, 10 uM APi2355, 10 uM APi2356 or with 20 uL of DMSO (negative control).

After 2 days of treatment, cells were washed once in cold, sterile HBSS. HBSS was removed, and 150 uL of lysis buffer with protease inhibitor cocktail was added to the cells. Cells were incubated with lysis buffer for 10 minutes. Cell lysates were scraped from the plates and collected. Cell lysates were then sonicated twice. Following sonication, the lysates were centrifuged at 13,000 RPM for 20 minutes. Lysates were then flash frozen in liquid nitrogen, thawed, vortexed, and centrifuged again at 13,000 RPM for 30 minutes. The supernatant was then collected and the pellet was discarded. The concentration of cell lysates was then determined by BCA assay.

Western blots were performed to evaluate the presence the effects of treatments. Briefly, 12 ug of each lysate was run on a 10% polyacrylamide gel. The gel was then transferred to a membrane and washed. Primary antibodies against smooth muscle actin (SMA) and Tubulin Results of the western blot can be seen in FIG. 1. The treatment for each of the lysates in the pictured lanes are: 1: Untreated, 2:10 µM LTI-03, 3: 90 µM LTI-03, 4: 10 µM APi2350, 5: 10 µM APi2354, 6: 10 µM APi 2355, 7: 10 µM APi2356, and 8: DMSO.

Figure 2:
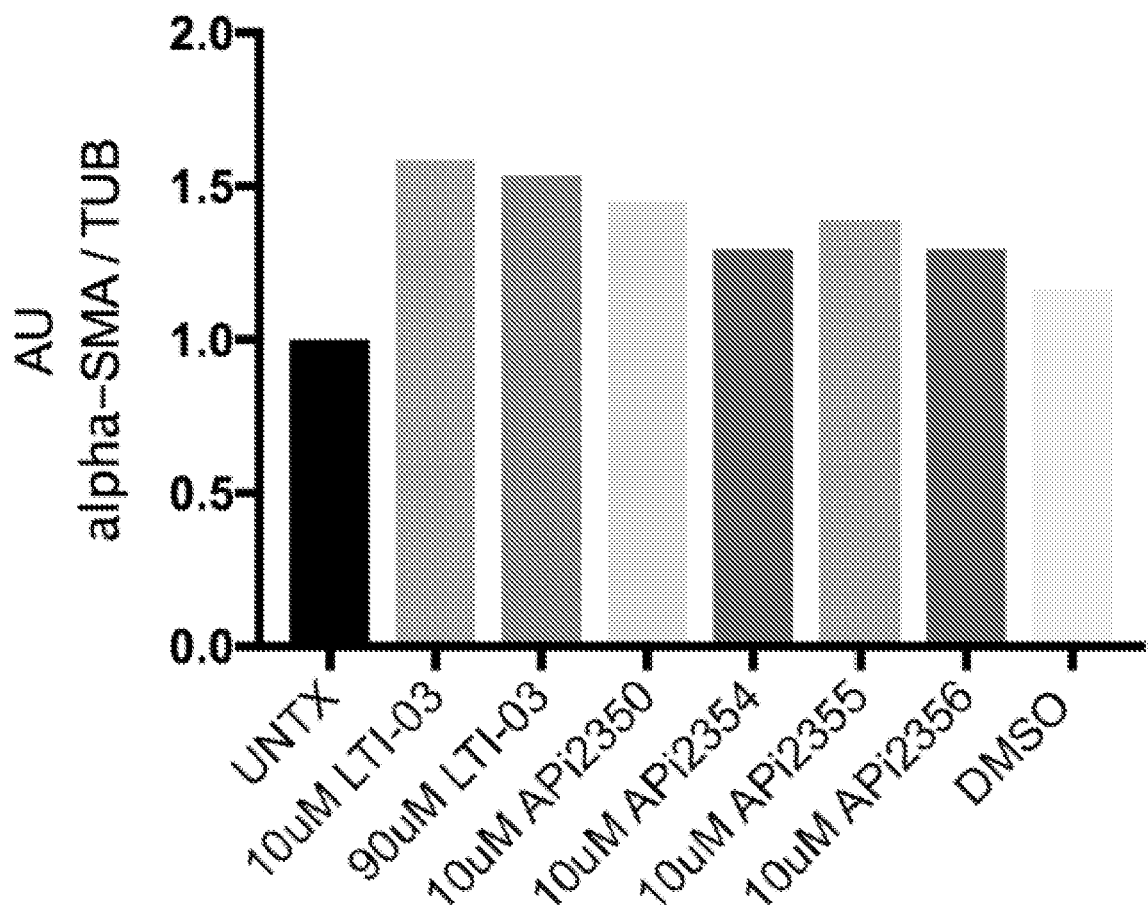
FIG. 2: Treatment with Cav-1 peptides increases SMA relative to tubulin in IPF cells. Graphical representation of the ratio of SMA to tubulin in cells receiving the indicated treatments.

Western blots were photographed and analyzed with ImageJ to determine a ratio of smooth muscle actin to tubulin (FIG. 2). As expected, LTI-03 elicited an increase in SMA production relative to tubulin. Treatment with Cav-1 peptides APi2350, APi2354, APi2355, and APi2356 all increased the expression of SMA relative to tubulin as well (FIG. 2).

Example 3—Cav-1 Peptides Preserve AEC2 Cells of Fibrotic Lung Biopsies

To assess the effect of Cav-1 peptide APi2355 (SEQ ID NO: 8) on AEC2 cell viability, surgical biopsies were obtained for the preparation of non-specific interstitial pneumonia precision cut lung slices (PCLS). One individual with non-specific interstitial pneumonia (NSIP) and another with end-stage IPF were processed. Lysotracker staining, which stains acidic compartments in live cells and selectively accumulates in the lamellar bodies of lung AEC2 cells (Van der Velden et al., 2013), was performed. Cav-1 peptide was suspended in DMEM/5% FBS, and PCLS slices (n=5 replicates/treatment group) were treated with 10, 100, or 500 µM LTI-03 or APi2355 (Var 55). Lysotracker staining (Green DND-26, Promega) was performed on NSIP PCLS 48 h after a single treatment. A strong dose-dependent increase in AEC2 cell viability was observed. In addition, lysotracker staining (Red DND-99, Promega) was performed on end-stage IPF on days 1, 2, 3, 5, and 7 following daily treatment with LTI-03 or APi2355. A dose-dependent increase in AEC2 cell viability was observed in an end-stage IPF biopsy treated for 7 consecutive days with LTI-03. The treatment effect for APi2355 (Var 55) was observed out to day 3.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

V. REFERENCES

The following references, to the extent that they provide exemplary procedural or other details supplementary to those set forth herein, are specifically incorporated herein by reference.

Bonelli, F. et al., *Int J Pept Protein Res.* 24(6):553-6 (1984).
Bundgaard H, Ed: *Design of Prodrugs*, Elsevier, Amsterdam, 1985
Current Protocols In Molecular Biology (F. M. Ausubel et al., eds., 1987)
Dordo et al, *J. Mol Biol,* 1999, 217, 721-739
Fults et al. (1991) *J Pharm Pharmacol* 43:726-8
Giannis et al., *Adv. in Drug Res.* 29:1-78 (1997).
Hruby, V J, Biopolymers 33:1073-1082 (1993)
Johnson et al., In: *Biotechnology and Pharmacy*, in Pezzuto et al., Chapman and Hall (Eds.), NY, 1993
Kyte and Doolittle, *J. Mol. Biol.,* 157(1):105-32, 1982.
McLean et al. (2000) *Anal Chem* 72:4796-804.
Meyer et al., *European Respiratory Journal,* 44: 1479-1503, 2014.
Moore et al., *Adv. in Pharmacol* 33:91-141 (1995)
Ralston et al., *Pediatrics,* 134(5): e1474-e1502, 2014.
Remington's Pharmaceutical Sciences, 18th edition, A. R. Gennaro, Ed., MackPubl., Easton, PA (1990).
S. French and B. Robson, *J. Mol. Evol.* 19(1983)171
Taylor et al, *J. Theor. Biol.* 119(1986); 205-218
U.S. Pat. No. 4,554,101
U.S. Pat. No. 5,277,175
U.S. Pat. No. 5,284,133
U.S. Pat. No. 5,355,872
U.S. Pat. No. 5,660,166
U.S. Pat. No. 5,797,389
U.S. Pat. No. 5,823,179
U.S. Pat. No. 5,889,155
U.S. Pat. No. 6,016,974
U.S. Pat. No. 6,041,776
U.S. Pat. No. 6,044,841
U.S. Pat. No. 6,241,159
U.S. Pat. No. 6,261,569
U.S. Pat. No. 6,261,569
U.S. Pat. No. 6,354,516
U.S. Pat. No. 6,357,671
U.S. Pat. No. 6,921,020
U.S. Pat. No. 6,926,208
U.S. Pat. No. 6,968,840
U.S. Pat. No. 6,978,941
U.S. Pat. No. 7,040,549
U.S. Pat. No. 7,083,112
U.S. Pat. No. 7,104,463
U.S. Pat. No. 7,360,536
U.S. Patent Publication No. 2002/0020409.
U.S. Patent Publication No. 2002/0020412
U.S. Patent Publication No. 2009/0134235
U.S. Patent Publication No. 2009/0304666
Vecellio None et al. (2001) *J Aerosol Med* 14:107-1
Verdini, A and Viscomi, G. C, *J. Chem. Soc. Perkin Trans.* 1:697-701, 1985.
Waldrep and Dhand, *Curr. Drug Deliv.,* 5(2):114-9, 2008.
Wawrzynczak and Thorpe, *Cancer Treat Res.,* 37:239-51, 1988.
Wiley, R A et al., *Med. Res. Rev.* 13:327-384, 1993.

What is claimed is:

1. A peptide comprising aaEGKASFTTFTVTKGSaa-NH2 (SEQ ID NO: 7) or Ac-aaEGKASFTTFTVTKGSaa-NH2 (SEQ ID NO: 8), wherein: "a" in SEQ ID NO: 7 or SEQ ID NO: 8 is D-alanine; wherein either amino acid sequence may optionally comprise at least one non-standard amino acid substitution; and the peptide is soluble in aqueous solution.

2. The peptide of claim 1, wherein the peptide sequence of SEQ ID NO: 7 further comprises at least one amino acid added to the N-terminus.

3. The peptide of claim 1, wherein the at least one non-standard substitution is ornithine substituted for lysine (K) in SEQ ID NO: 7 or SEQ ID NO: 8.

4. The peptide of claim 1, wherein the peptide of SEQ ID NO: 7 further comprises an N-terminal modification.

5. The peptide of claim 4, wherein the N-terminal modification is acylation.

6. The peptide of claim 1, wherein the peptide comprises the amino acid sequence of aaEGKASETTFTVTKGSaa-NH2 (SEQ ID NO: 7).

7. The peptide of claim 1, wherein the peptide comprises the amino acid sequence Ac-aaEGKASFTTFTVTKGSaa-NH2 (SEQ ID NO: 8).

8. A composition comprising a peptide of claim 1.

9. The composition of claim 8, wherein the peptide is at least 98% pure.

10. The composition of claim 8, wherein the composition is formulated as a dry powder.

11. A peptide consisting of Ac-aaEGKASFTTFTVTKGSaa-NH2 (SEQ ID NO: 8).

* * * * *